United States Patent [19]
Monji et al.

[11] Patent Number: 4,780,409
[45] Date of Patent: Oct. 25, 1988

[54] THERMALLY INDUCED PHASE SEPARATION IMMUNOASSAY

[75] Inventors: Nobuo Monji; Allan S. Hoffman, both of Seattle; John H. Priest, Everett; Raymond L. Houghton, Kirkland, all of Wash.

[73] Assignee: Genetic Systems Corporation, Seattle, Wash.

[21] Appl. No.: 854,831

[22] Filed: Apr. 28, 1986

Related U.S. Application Data

[63] Continuation-in-part of Ser. No. 729,510, May 2, 1985, abandoned.

[51] Int. Cl.$^4$ .............................. G01N 33/53/33/539
[52] U.S. Cl. ...................................... 435/7; 436/519; 436/539; 436/540; 436/824; 436/827
[58] Field of Search ................... 435/7; 436/501, 519, 436/539, 540, 824, 827

[56] References Cited

U.S. PATENT DOCUMENTS

| | | |
|---|---|---|
| 3,817,837 | 6/1974 | Rubenstein et al. |
| 4,065,310 | 12/1977 | Dujardin et al. ............... 525/54.1 X |
| 4,088,538 | 5/1978 | Schneider. |
| 4,231,999 | 11/1980 | Carlsson et al. ..................... 435/7 X |
| 4,281,061 | 7/1981 | Zuk et al. ............................ 435/7 X |
| 4,371,515 | 2/1983 | Chu ................................ 436/827 X |
| 4,469,796 | 9/1984 | Axeu et al. ...................... 436/540 X |
| 4,493,793 | 1/1985 | Chu ................................ 436/827 X |
| 4,511,478 | 4/1985 | Nowinski et al. ............... 436/827 X |
| 4,522,922 | 6/1985 | Carro et al. ..................... 436/540 X |
| 4,530,900 | 7/1985 | Marshall ........................ 436/539 X |
| 4,609,707 | 9/1986 | Nowinski et al. ............... 436/827 X |
| 4,711,840 | 12/1987 | Nowinski et al. ............... 436/539 X |

FOREIGN PATENT DOCUMENTS 0124050 11/1984 European Pat. Off.

OTHER PUBLICATIONS

Charles et al., *Biotech. Bioeng.* 16:1553-1556, 1974.
Margolin et al., *Biotech. Bioeng.* 24:237-240, 1982.
*Water Soluble Synthetic Polymers: Properties and Behavior,* Molyneux, CRC Press, Boca Raton, Florida, 1983 (table of contents only).
*Chemistry and Technology of Water-Soluble Polymers,* C. A. Finch ed. Plenum Press, New York, N.Y., 1983 (table of contents, only).

*Primary Examiner*—Sidney Marantz
*Assistant Examiner*—Richard Wagner

[57] ABSTRACT

An immunoassay in which a thermally induced phase separation is used to effect the separation of specifically bound reactants from free reactants is disclosed. A first reactant is conjugated to a temperature-sensitive polymer to form a polymer/reactant conjugate, and a second reactant is conjugated to a reporter to form a reporter/reactant conjugate. The polymer/reactant, reporter/reactant, and biological fluid samples suspected of containing the analyte are admixed in solution at a temperature other than that at which the polymer will precipitate. Specific binding is allowed to occur, thereby forming a ternary complex. The salt concentration of the adjusted solution is then adjusted to a concentration sufficient to cause the complex to precipitate from the solution, the amount of reporter activity in the precipitated complex or in the solution measured and the presence and/or concentration of the analyte therefrom determined. Alternatively, the first reactant may be conjugated to a monomer and subsequently copolymerized with additional monomers to yield a temperature-sensitive copolymer. Multiple analyses may also be performed on a single sample by choosing a variety of polymers, each polymer having a different specific binding partner conjugated thereto and a different critical solution temperature. By altering the temperature and/or the salt concentration of the solution incrementally, the reporter associated with each of the complexes precipitated with each temperature or concentration increment may be measured, and the presence and-/or concentration of each of the analytes determined.

109 Claims, 7 Drawing Sheets

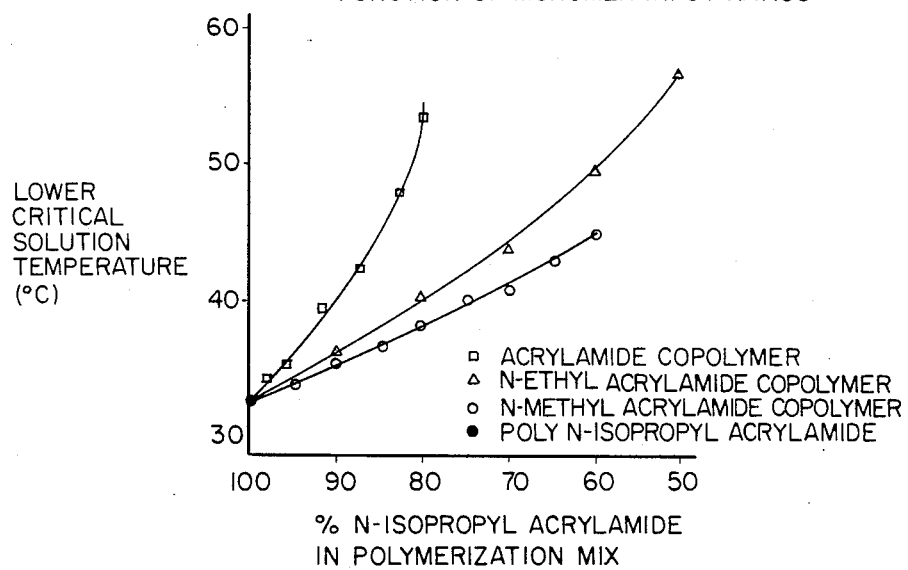
FIG. 9 LOWER CRITICAL SOLUTION TEMPERATURES OF COPOLYMERS OF N-ISOPROPYL ACRYLAMIDE WITH OTHER N-ALKYL ACRYLAMIDES AS A FUNCTION OF MONOMER INPUT RATIOS
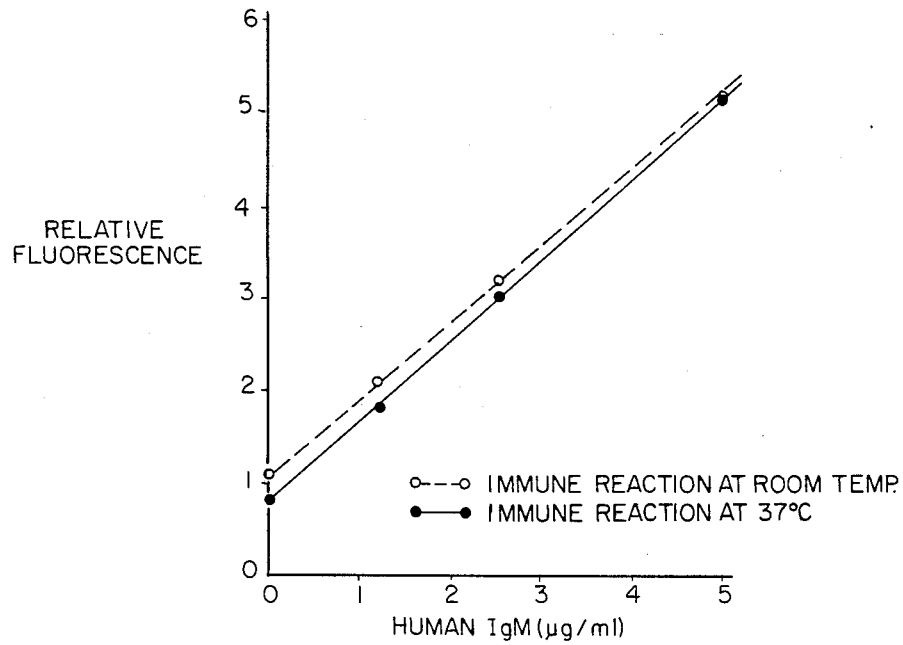
FIG. 10

DUAL ANALYTE ASSAY FOR HUMAN IgG AND IgM USING THERMAL PRECIPITATION AT TWO TEMPS.

STANDARD CURVE FOR DETECTION OF CHLAMYDIA TRACHOMATIS ELEMENTARY BODIES

FIG. 13

REACTIVITY OF WATER SOLUBLE POLYMERS WITH
CHLAMYDIA TRACHOMATIS ELEMENTARY BODIES

AQUEOUS
poly-N-isopropylacrylamide
$4 \times 10^5$

BENZENE
poly-N-isopropylacrylamide
$4 \times 10^5$

THF
poly-N-isopropylacrylamide
$4 \times 10^5$

BENZENE (9) : THF (1)
poly-N-isopropylacrylamide
$4 \times 10^5$

OD450

% POLYMER (w/v)

THERMALLY INDUCED PHASE SEPARATION IMMUNOASSAY

CROSS-REFERENCE TO RELATED APPLICATION

This application is a continuation-in-part of applicant's copending application Ser. No. 729,510, filed May 2, 1985, which application is now abandoned.

TECHNICAL FIELD

The present invention relates generally to immunoassay methods, and more particularly to an immunoassay in which a thermally induced phase separation is used to effect the separation of specifically bound reactants from free reactants.

BACKGROUND ART

Immunoassays have found widespread application in the field of clinical diagnostics for the detection and measurement of drugs, vitamins, hormones, proteins, metabolites, microorganisms, and other substances of interest (analytes) in biological and non-biological fluids. Typically, these analytes occur in micromolar ($10^{-6}$M) or less concentration.

Immunoassays generally incorporate antibodies and antigens as reactants, at least one of which is labeled with a signal-producing compound (e.g., radioisotope, fluorophore, enzyme, etc.). Following mixture with the sample and incubation, specific antibody/antigen reactions occur (specific binding). The reaction mixture is subsequently analyzed to detect free and specifically bound labeled reactant, enabling a measurement of the analyte in the sample.

Immunoassays can be divided into two general categories, homogeneous and heterogeneous. In a homogeneous immunoassay, the signal emitted by the specifically bound labeled reactant is different from the signal emitted by the free labeled reactant. Hence bound and free can be distinguished without physical separation.

The archetypal homogeneous immunoassay is the enzyme-multiplied immunoassay technique (EMIT) which is disclosed in U.S. Pat. No. 3,817,837. In this technology, analyte present in patient sample and analyte/enzyme conjugate compete for a limited amount of anti-analyte antibody. Specific binding of antibody to the conjugate modulates its enzymatic activity, hence the amount of enzyme activity is proportional to the amount of analyte in the sample.

Homogeneous immunoassays have the advantages of being rapid, easy to perform, and readily amenable to automation. Their principal disadvantages are that they are relatively prone to interferences, are generally limited to low molecular weight analytes, and are generally limited in sensitivity to approximately $10^{-9}$M.

In a heterogeneous immunoassay, the signal emitted by the bound labeled reactant is indistinguishable from the signal emitted by the free labeled reactant; therefore, a separation step is required to distinguish between the two. Typical heterogeneous immunoassays include the radioimmunoassay (RIA) and the enzyme-linked immunosorbent assay (ELISA).

In the RIA, radiolabeled analyte and analyte present in patient sample compete for a limited amount of immobilized (solid-phase) anti-analyte antibody. The solid phase is washed to remove unbound, labeled analyte, and either the bound or the free fraction is analyzed for the presence of labeled reactant. ELISA assays are performed analogously. In the latter case though, the signal is an enzyme instead of a radioisotope. Heterogeneous immunoassays typically employ at least one reactant immobilized on a solid phase. Solids used to immobilize reactants in immunoassays have included controlled pore glass and preformed polymers, such as polyvinyls, polyacrylamides, polydextrans, and polystyrenes. Numerous separation methods are known in the art and have been used in heterogeneous immunoassays. These include centrifugation, microfiltration, affinity chromatography, and gel-permeation chromatography. Since the kinetics of reaction between an immobilized antibody (or antigen) and its binding site tend to be slower than the kinetics of the same reaction occurring in solution, long incubation times are frequently required. When the multiple wash steps often needed are considered, it can be appreciated that heterogeneous assays tend to be time-consuming and labor-intensive. However, they are in general more sensitive than homogeneous assays and less prone to interferences, since interfering substances can be removed in the wash step(s).

More recently, EP No. 124,050 by Jolley, discloses a method of solid phase immunoassay in which the analyte is reacted with an immunoreactant immobilized on water-insoluble particles in a substantially suspended state and thereafter concentrated by mirofiltration to a volume substantially less than the volume of the original sample. This method suffers from the same disadvantages associated with all solid phase-based immunoassays, namely, slow reaction kinetics and high nonspecific binding.

In addition to the immunoassays described above, there have more recently been a number of efforts directed toward the use of reversibly soluble "complexes" within the context of immunoassays. Representative of the earlier work with reversibly-soluble enzyme catalysts is the research conducted by Charles, et al., Biotech., Bioeng., 16: 1553 (1974), which discloses the synthesis of reversibly soluble lysozyme-alginic acid "complexes" by first reacting alginic acid with CNBr and then contacting the activated acid with a solution of lysozyme. The resultant complex is soluble above pH 4.0 and can be rendered insoluble by lowering the pH below 3.0. Because the pH optimum of lysozyme is 8.5, however, the pH change required to effect insolubilization is quite large (pH being on a logarithmic scale). Such a large change, with concomitant changes in ionic strength, would be unlikely to be well tolerated by the majority of biologically active materials. Furthermore, most specific binding pairs will dissociate at a pH of 3; thus the method as disclosed is not widely applicable for catalysis and is not applicable at all to specific binding assays.

An improvement over the complexes of Charles, et al., is the work of Margolin et al. (Biotech., Bioeng., 24: 237 (1982)), which discloses the synthesis of reversibly soluble enzyme-polyelectrolyte complexes by first reacting an enzyme with an activated polycation and then reacting the enzyme-polycation conjugate with a polyanion. Solubility of the resultant complexes is a function of pH or salt concentration. These complexes overcome some of the disadvantages of Charles et al., supra, in tht the precipitation occurs over a narrower and less extreme range of pH or salt concentration. Nonetheless, the method remains cumbersome due to the need to complex oppositely charged polyelectrolytes and is expected to be prone to nonspecific binding via ionic interactions with the complex.

One of the first direct applications of the use of reversibly-soluble complexes to immunoassays is disclosed in U.S. Pat. No. 4,088,538, issued to schneider. The Schneider patent discloses a process for using and preparing a reversibly soluble, enzymatically active enzyme product which consists of an enzyme covalently bonded to a water-soluble organic polymer selected from polyacrylic acid, dextran, carboxymethyl cellulose, and polyethylene glycol, which have carboxyl or amino side groups that impart to the complex its reversible solubility. Insolubilization is effected by a change in pH or calcium ion concentration. However, the suitability of this method to the immunoassay of substances in biological fluids is uncertain.

Another application similar to that disclosed within Schnieder is U.S. Pat. No. 4,530,900, issued to Marshall et al. Marshall et al. discloses the use of reversibly soluble polymers of alginic acid to which antibodies or antigens have been covalently attached in an enzyme immunoassay. Polymers which find utility in this method are those which have free carboxyl groups and which can be precipitated from solution by a change in pH or by the addition of certain metal ions, such as calcium. The enzymatic signal is developed in solution after separation of bound from free labeled component and redissolution of the precipitate.

There is a need in the art, however, for an immunoassay method which is sensitive to sub-micromolar concentrations of analyte, which has fast-reaction kinetics, which permits multiple analyses to be performed on a single sample, and which is readily amenable to automation. The present invention fulfills this need, and further provides other related advantages.

DISCLOSURE OF INVENTION

Briefly stated, the present invention discloses a method for determining the presence and/or concentration of an analyte in a biological fluid sample. Essential features of the method include: (a) conjugating a first reactant which is capable of specifically binding with the analyte to a temperature-sensitive polymer to form a polymer/reactant conjugate; (b) conjugating a second reactant which is capable of specifically binding with the analyte to a reporter to form a reporter/reactant conjugate; (c) admixing in solution the polymer/reactant, reporter/reactant and the biological fluid sample suspected of containing the analyte at a temperature other than that at which the polymer will precipitate, such that specific binding occurs between the first and second reactants and the analyte, thereby forming a ternary complex; (d) adjusting the salt concentration of the admixed polymer/reactant, reporter/reactant, and analyte containing sample solution to a concentration sufficient to cause the complex to precipitate from the solution; and (e) measuring the amount of reporter activity in the precipitated complex or in the solution and therefrom determining the presence and/or concentration of the analyte. The method may also include, after the step of adjusting, separating the precipitated complex from the solution as by centrifugation, microfiltration, or gel-permeation chromatography.

The polymer may be one characterized by a lower critical solution temperature, thereby precipitating upon heating the solution above the temperature, or may be characterized by an upper critical solution temperature, thereby precipitating upon cooling the solution below the temperature. Further, the polymer may be a copolymer formed from monomers selected to achieve a desired critical solution temperature. The first and second reactants are typically antibodies or antigens, although other reactants, such as lectins, receptors, transport proteins and non-immunoblobulin antibody-binding proteins may be used. Through the use of this method, the presence and/or concentration of a variety of analytes may be determined, such as drugs, vitamins, hormones, proteins, metabolites, cells, viruses, and microorganisms. Reporters which may be used include enzymes, fluorophores, radioisotopes, luminescers, and dye particles.

Another aspect of the invention discloses a method for determining the presence and/or concentration of an analyte in a biological fluid sample in which the reactant is conjugated to a monomer and copolymerized with additional monomers to yield a temperature-sensitive copolymer/reactant. Subsequent to conjugating a second reactant which is capable of specifically binding with the analyte to a reporter to form a reporter/reactant conjugate, the copolymer/reactant, reporter/reactant, and biological fluid sample suspected of containing the analyte are admixed in solution at a temperature other than that at which the copolymer will precipitate. Specific binding between the first and second reactants and the analyte is allowed to occur, thereby forming a ternary complex. The salt concentration of the admixed copolymer/reactant, reporter/reactant, and analyte containing sample solution is then adjusted to a concentration sufficient to cause the complex to precipitate from the solution. The amount of reporter activity in the precipitated complex or in the solution may then be measured and therefrom the presence and/or concentration of the analyte determined.

A third aspect of the present invention discloses a method for conducting multiple analyses on a single biological fluid sample suspected of containing one or more analytes. The method generally comprises: (a) conjugating a plurality of selected first reactants capable of specific binding with one of the analytes to a plurality of temperature-sensitive polymers, each of the first reactants being conjugated to a polymer having a different critical solution temperature, thereby forming multiple polymer/reactant conjugates; (b) conjugating a plurality of selected second reactants capable of specifically binding with one of the analytes to one or more reporters to form multiple reporter/reactant conjugates; (c) admixing in solution the multiple polymer/reactant, multiple reporter/reactant, and the biological fluid sample suspected of containing one or more analytes at a temperature other than that at which any of the polymers will precipitate, such that specific binding occurs between the reactants and the analytes, thereby forming a plurality of ternary complexes; (d) adjusting the salt concentration of the admixed polymer/reactant, reporter/reactant, and analyte sample containing solution incrementally such that the complex precipitated with each concentration increment can be separated from the solution prior to the precipitation of a complex with a different critical solution temperature; and (e) measuring the amount of reporter activity in each of the precipitated complexes or in the solution and therefrom determining the presence and/or concentration of each of the analytes.

Alternatively, the conditions of the sample containing solution may be modified by utilizing various combinations of incubation and adjustment of the salt concentration, thereby selectively precipitating polymers having different critical solution temperatures.

Yet another aspect of the present invention discloses a method for determining the presence and/or concentration of a member of the genus Chlamydia in a biological fluid sample. The method generally comprises: (a) providing a temperature-sensitive polymer that is capable of binding to the elementary bodies of a member of the genus Chlamydia; (b) conjugating a first reactant which is capable of specifically binding with the chalmydial member to a reporter to form a reporter/reactant conjugate; (c) admixing in solution the polymer, reporter/reactant and the biological fluid sample suspected of containing the chlamydial member at a temperature other than that at which the polymer will precipitate, such that binding occurs between the polymer and the first reactant and the chlamydial member, thereby forming a ternary complex; (d) incubating the admixed polymer, reporter/reactant, and chlamydial member containing sample solution at a temperature sufficient to cause the complex to precipitate from the solution; and (e) measuring the amount of reporter activity in the precipitated complex or in the solution and therefrom determining the presence and/or concentration of the member of the genus Chlamydia. This method is particularly well suited to determining the presence and/or concentration of the species *Chlamydia trachomatis*. In this regard it is preferable to use a suitable antibody as the first reactant.

Other aspects of the invention will become evident upon reference to the following detailed description and attached drawings.

BRIEF DESCRIPTION OF THE DRAWINGS

FIG. 9 graphically depicts the lower critical solution temperature (LCST) of several copolymers as a function of increasing concentration of acrylamide and N-substituted acrylamide.

FIG. 10 depicts a pair of standard curves for determining human IgM after incubation at two different temperatures.

FIG. 13 graphically depicts the reactivity of chalmydia elementary bodies with several water soluble polymers.

BEST MODE FOR CARRYING OUT THE INVENTION

Figure 1:
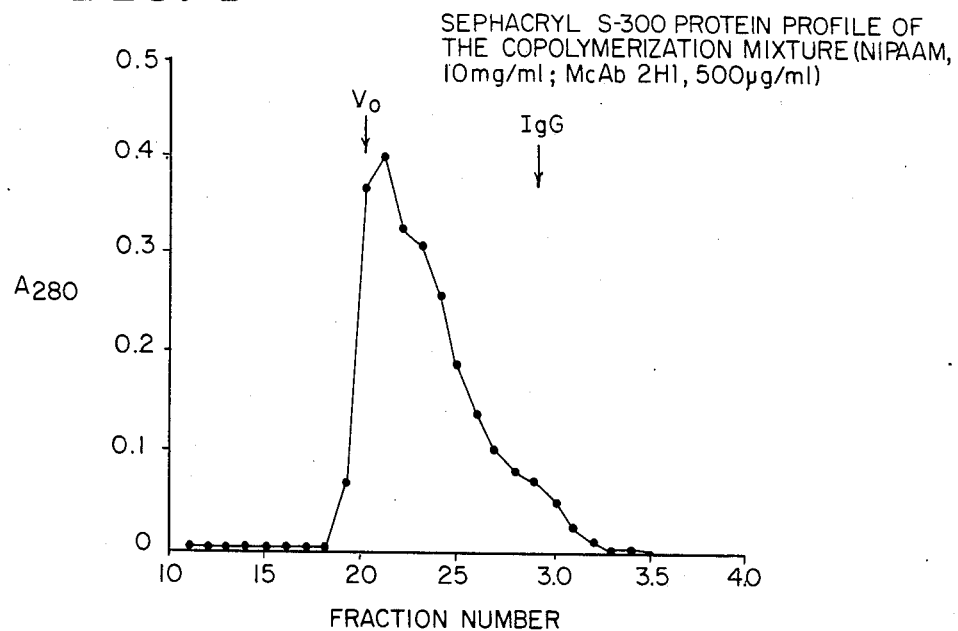
FIG. 1 depicts graphically the purification of a polymer/reactant conjugate by gel-permeation chromatography.

Prior to setting forth the invention, it may be helpful to an understanding thereof to set forth definitions of certain terms to be used hereinafter.

Analyte—is a substance or group of substances, the presence or amount of which it is desired to determine.

Biological fluids—are blood, blood serum, blood plasma, urine, feces, cerebrospinal fluid, saliva, sputum, cell- and tissue-derived extracts, etc., in which the analyte is suspected of being contained.

Reactants—are naturally occurring or synthetic substances, typically antigens and antibodies, which are capable of recognizing and specifically binding to each other.

Antigen—as used herein includes molecules which themselves may induce antibodies as well as small molecules which are not capable of eliciting antibody production unless they are coupled to a carrier (e.g., haptens).

Epitope—is any antigenic determinant.

Specific binding reactions—are reactions characterized in that the reactants have an affinity for each other of at least $10^{-6}$M, more often at least $10^{-8}$M, and preferably at least $10^{-9}$M.

Reporter—is any substance which is capable of producing a detectable signal, either alone or in combination with other reagents, such as, for example, radioisotopes, fluorephores, chromophores, liminescers, and enzymes.

Although the following discussion pertains primarily to the immunoassay of analytes in biological fluids, it will be appreciated that there are numerous disciplines which require the assay of fluid samples for the presence or amount of organic substances. These disciplines include, for example, food preparation and environmental quality control.

Reversibly Soluble Polymers

The methods of this invention for the immunoassay of analytes in biological fluids utilize conjugates of reactants with polymers exhibiting either an upper or a lower critical solution temperature (polymer/reactant conjugates) and conjugates of reactants with signal-producing compounds (reporter/reactant conjugates).

Certain water-soluble polymers are known to precipitate when a critical solution temperature is reached (Molyneux, *Water Soluble Synthetic Polymers: Properties and Behavior*, CRC Press, Boca Raton, Fla., 1983). The majority of polymers exhibit de-mixing behavior (phase separation) upon cooling. Such behavior is called "$\theta$ behavior" and the temperature at which de-mixing occurs is referred to as the upper critical solution temperature (UCST). However, certain polymers exhibit de-mixing behavior (phase separation) on heating. Such behavior is called "$\theta_+$ behavior" and the temperature at which de-mixing occurs is referred to as the lower critical solution temperature (LCST).

Among polymers having an upper critical solution temperature are the following: polyethylene glycol (PEG), polyacrylic acid (PAA), polymethacrylamide (PMAAm), and polyvinyl alcohol (PVA). Among polymers which exhibit a lower critical solution temperature are the following: polyvinyl methylether (PVME), polyvinylmethyl oxazolidone (PVMO), polymethacrylic acid (PMAA), poly-N-isopropylacrylamide (PNIPAAm), hydroxypropyl cellulose (HPC), and methyl cellulose (MC). [Franks, in C. A. Finch, ed., *Chemistry and Technology of Water-Soluble Polymers*, New York, Plenum Press, 1983, p. 157] Any polymer or copolymer or monomers thereof, be they naturally occurring, synthetic, or semi-synthetic, which exhibit de-mixing behavior upon a change in temperature can be conjugated to a reactant and used in the immunoassays of this invention.

Particularly preferred are polymers or monomers of N-isopropyl acrylamide, and acrylamide copolymers thereof.

The critical solution temperature can be chosen to be almost any temperature desired by copolymerizing various monomers in different proportions to achieve copolymers having the desired critical solution temperature. For example, N-isopropyl acrylamide monomers can be copolymerized with acrylamide monomers where the proportion of acrylamide monomers ranges between 1% and about 10%, in order to produce copolymers which exhibit LCSTs ranging between about 35° C. and 55° C. In addition to acrylamide monomers, several other monomers may be copolymerized with N-isopropyl acrylamide monomers in order to produce particularly desirable copolymers. For instance, such monomers include N-ethyl acrylamide monomers, N-methyl acrylamide monomers, and N-isopropyl acrylamide monomers. Purification of the desired species is readily accomplished by raising the temperature above the LCST (or lowering it below the UCST) to effect precipitation.

The critical solution temperature of a given polymer or copolymer may be affected by the presence of various solutes (Eliassaf, J., Applied Polymer Science, 22: 873, 1978), such as ions and proteins, which may be encountered in biological fluids. The critical solution temperature may also be affected by the nature and number of specific binding partners conjugated to the polymer. These effects can be determined empirically.

It is preferred to choose a polymer or copolymer the critical solution temperature of which is not affected by substances commonly encountered in biological samples or added thereto for purposes of assay. Such substances may include urea, creatinine, anti-coagulants, ionic and non-ionic detergents, and N-acetylcysteine.

Polymer/Reactant Conjugates

Typically, the reactant is an antibody or an antigen; however, other reactants are known in the art, including, for example, lectins, receptors, transport proteins, and non-immunoglobulin antibody-binding proteins such as staphylococcal protein A. Where the reactant is an antibody, either monoclonal or polyclonal antibodies can be used. Prior to conjugation, the antibody will in general be at least partially purified by methods well known in the art.

The reactant can be conjugated to a monomer and copolymerized with additional monomers to form a copolymer which exhibits either an upper or a lower critical solution temperature, depending upon its composition. For example, the reactant can be conjugated to an activated ester of a monomer, such as the N-hydroxysuccinimide ester of acrylic acid or vinyl benzoate, and the resultant monomerized reactant copolymerized with other monomers, such as N-isopropylacrylamide.

Alternatively, the temperature-sensitive polymer can be preformed (pre-polymerized) and the reactant conjugated to the preformed polymer by conventional chemistry. For example, an activated ester of the reactant can be conjugated via carbodiimide to reactive groups on the polymer.

Purification of the polymer/reactant conjugate can be accomplished by any of a variety of methods well known in the art. For example, the conjugate can be purified by gel-permeation chromatography. Alternatively, it can be purified by serial precipitation of the polymer/reactant conjugate. If the latter method is used, care must be taken to ensure that the reactant is not denatured.

Gel-permeation chromatography and serial precipitation will suffice to remove free antibody from antibody-conjugated polymer but will not remove free polymer from the mixture. Separation of free polymer from antibody-conjugated polymer can be accomplished by chromatography on hydroxylapatite (HAP). The free polymer will pass through the column at conditions under which the antibody-conjugated polymer will bind to the column. The conjugate can subsequently be eluted by changing the ionic strength of the buffer in which chromatography is performed.

Reporter/Reactant Conjugate

In addition to a polymer/reactant conjugate, a reporter/reactant conjugate is required. The reporter can be chosen from any of those known in the art, including enzymes, fluorophores, radioisotopes, luminescers, dye particles, etc. Some suitable fluorophores include fluorescein, rhodamine, phycoerythin, and nile blue. Among preferred enzymes are horseradish peroxidase (HRP), $\beta$-galactosidase $\beta$-GAL), and alkaline phosphatase (AP).

Phase Separation

Separation of free from specifically bound reporter/reactant conjugate is effected by a phase separation reaction. In general, that phase separation reaction is induced by a change in temperature, although other effectors, such as pH, salt concentration, etc., are possible. In general, that phase separation is also reversible, i.e., the polymer/reactant conjugate will go back into solution when the temperature is lowered below the LCST or raised above the UCST.

It is usually preferred that phase separation be effected by a change in temperature. The temperature of a reaction mixture is easily controlled, whereas the pH or salt concentration may vary depending on the source and composition of the sample. Further, changes in salt concentration may result in the co-precipitation of undesired components of the reaction mixture, particularly when the reaction mixture is a complex biological fluid. Also, the temperature of a reaction mixture can be varied rapidly and precisely without the addition of exogenous reactants, thus reducing the complexity of the assay.

Where temperature control is not achievable, or where it is not desirable to significantly alter the temperature, salt concentration can be employed in order to effectively lower the critical solution temperature of the polymer. For example, the assays of this invention can be adapted to instrumentation which is not thermostatted, such as the flow microfluorimeter. It has been found that ammonium sulfate (14–25% of saturation) will selectively precipitate the polymer or copolymer conjugates of this invention without substantially precipitating other components of the reaction mixtures. If the salt is present in greater than 35% of saturation, polyclonal antibody would be expected to precipitate, while monoclonal antibody would be expected to precipitate at greater than 50% of saturation. In addition to ammonium sulfate, other sulfates such as sodium sulfate may be used. Other suitable salts include sodium carbonate, potassium carbonate, and sodium phosphate. In general, it is preferable to utilize salts at a concentration of greater than or equal to approximately $\geq 0.25$M. This will generally lower the LCST to approximately 25° C. Salt-induced precipitation is also useful for purification of the polymer conjugates from free antibody. Briefly, subsequent to the serial salt-induced precipitation of the polymer/antibody conjugate, the conjugate may be purified by chromatographic methods, such as by hydroxylapatite chromatography.

In general, it is preferred that the antigen/antibody (or other specific binding) reaction take place at temperatures between about 0° C. and 55° C., more often between 22° C. and 45° C. The critical temperature of the polymer can be any temperature above or below the temperature at which the specific binding reaction occurs and will usually be at least 1° C., and more often 5°–10° C., above or below that temperature. The critical solution temperature, in any case, must be less than the temperature at which specific binding pairs dissociate. Similarly, the critical solution temperature should also be less than the temperature at which proteins denature. For example, if poly-N-isopropylacryamide is chosen as the polymer, specific binding reactions might be carried out at temperatures of about 30° C., as the critical solution temperature for this polymer is about 31° C. (Eliassaf et al., Polymer 3: 555, 1962).

In many instances, specific binding reactions can be enhanced by raising the temperature to between 37° C. and 45° C. It has been found that PolyNIPAAm/antibody conjugates purified by chromatography on hydroxylapatite do not phase separate macroscopically at temperatures above the LCST (31° C.) unless carrier (unconjugated) polymer is added. Thus specific binding reactions can be carried out at 37° C. using this purified material and phase separation subsequently achieved by the addition of carrier. Alternatively, one can use an acrylamide copolymer of NIPAAm which has an LCST greater than 37° C.

Assay Modes

The immunoassays of the present invention can be performed in any of several configurations. These can include competitive, sandwich, and non-competitive immunoassay configurations. In every case, the analyte of interest can be either an antigen or an antibody. In every case, either reactant (i.e., antigen or antibody) can be conjugated to either the polymer or to the reporter. The various possible configurations in which immunoassays can be performed are reviewed extensively in *Enzyme Immunoassay*, E. T. Maggio, ed., CRC Press, Boca Raton, Fla. (1980), and in numerous other publications.

The assays of the present invention can be performed heterogeneously or homogeneously. If heterogeneously, the precipitated polymer can be separated from solution by centrifugation, microfiltration, etc. The precipitate can be washed one or more times, if desired, by dissolution in an appropriate buffer, followed by re-precipitation. If homogeneously, the assay can be performed, for example, as an agglutination assay. Alternatively, the critical solution temperature can be affected by the interaction of different polymers, thus affording a homogeneous assay system.

Multiple analyses can be performed on a single sample by choosing a variety of polymers, each polymer having a different specific binding partner conjugated thereto and a different critical solution temperature. The sample would be warmed or cooled incrementally, the precipitate formed with each temperature increment allowed to separate from solution, and the reporter associated therewith measured. Alternatively, the salt concentration of the sample could be adjusted incrementally, and the precipitate formed with each concentration increment allowed to separate from solution, and the reporter associated therewith measured. As a further alternative, the conditions of the sample may be selectively modified by various combinations of incubation and adjustment of the salt concentration in order to selectively precipitate polymers having different critical solution temperatures. With respect to this last alternative, it is preferable to begin with incubating the sample and then subsequently adjusting the salt concentration of the sample.

Multiple analyses can also be performed on a sample by choosing a variety of reporters, each reporter having a different specific binding partner conjugated thereto. The polymer precipitate formed would then be analyzed for each reporter. Similarly, many multiple analyses could also be performed on a sample by selecting both a variety of polymers and a variety of reporters.

Thermally induced phase separation immunoassays offer many advantages over prior art immunoassays. First, specific binding reactions occur in solution rather than on a solid phase, hence the reaction kinetics are more favorable, leading to reduced incubation times.

Second, nonspecific binding is much lower than in conventional solid phase immunoassays, such as that taught by Jolley. This is due to the fact that conventional solid phases are hydrophobic and will adsorb proteins onto their surfaces. Further, in a typical prior art immunoassay, the solid phase is present throughout the assay, maximizing the opportunity for nonspecific binding to occur.

Third, formation of the solid phase, i.e., precipitation, is reversible. Thus nonspecific entrapment of signal can be virtually eliminated by serial precipitation and redissolution.

Fourth, a concentration effect is obtained by virtue of the fact that the precipitated polymer can be redissolved in a substantially smaller volume than the original volume of the assay. The ultimate concentration effect is obtained by measuring the signal in the solid, i.e., percipitated phase.

Fifth, signal generation can occur in either phase. This is particularly advantageous if the reporter is an enzyme, where diffusion of the substrate into the precipitate may be rate-limiting.

The following examples are provided by way of illustration rather than implying any limitation of the present invention.

EXAMPLE I

Synthesis and Characterization of Antibody-Conjugated PolyNIPAAm

A. Preparation of monomer-conjugated monoclonal antibody (MAb)

A mouse monoclonal antibody to the kappa light chain of human immunoglobulin was purified from ascites fluid by ion exchange chromatography and dialyzed overnight against 0.29M carbonate buffer, pH 9.3. To the dialyzed, 5 mg/mL solution, an 8-fold molar excess of the N-hydroxysuccinimide ester of acrylic acid was added (2 mg active ester/ml DMSO). The resultant mixture was incubated for 60 minutes at 37° C., then passed through a column of Sephadex G-25 which had been equilibrated with phosphate-buffered saline (PBS), pH 7.4. The fractions of the eluant which contained antibody were pooled and stored at −20° C. The number of monomers per antibody was determined by isoelectric focusing to be approximately 6.

An aliquot of this monomer-conjugated $MAb_m$ was further reacted with a 25-fold molar excess of fluorescein isothiocyanate (isomer II, 10 mg/ml in DMSO). Excess unconjugated fluorescein isothiocyanate was removed by gel filtration on a Sephadex G-25 column. The resultant double-conjugated MAb ($MAb_{m,f}$) was stored at −20° C.

B. Copolymerization of $MAb_m$ with N-isopropyl acrylamide (NIPAAm)

To 1.6 m of 1.25% NIPAAm (w/v) in PBS, 0.2 ml of $MAb_m$ (8.4 mg/ml) was added. Polymerization was initiated by the formation of free radicals using 0.1 ml of 100 mM ammonium persulfate and 0.1 ml of 0.8M N,N,N',N'-tetramethylethylenediamine (TEMED). The reaction mixture was incubated for three hours at room temperature, at which time the polyNIPAAm/MAb conjugate was isolated by one of two different procedures:

1. Isolation of polyNIPAAm/MAb conjugate by gel-permeation chromatography

The reaction mixture was applied to a Sephacryl S-300 gel-permeation column (1.0×50 cm) to separate the polymer-conjugated MAb from the unbound MAb. The void volume fractions which contained polyNIPPAm/MAb conjugate (>$10^6$ molecular weight) were pooled and used for subsequent studies. A typical elution profile is shown in FIG. 1.

2. Isolation of polyNIPAAm/MAb conjugate by serial thermal precipitation

The polyNIPAAm/MAb conjugate was isolated by serially precipitating it from solution was follows: The reaction mixture (1% in polyNIPAAm) was diluted 10-fold with PBS and aliquoted into 1.5 ml Eppendorf tubes. The tubes were incubated for ten minutes at 37° C. to precipitate the polymer, then centrifuged for five minutes at 4,000×g at 37° C. The supernatant was withdrawn while the tube was immersed in a 37° C. water bath. The precipitate was then redissolved in ice-cold PBS and the cycle repeated for a total of three times. After the third precipitation, the precipitate was dissolved in 1/10 the original volume of PBS. The contents of the tubes were pooled and stored at 4° C. (1% polyNIPAAm/MAb).

3. Isolation of polyNIPAAm/MAb conjugate by serial salt-induced precipitation

The reaction mixture was diluted to 6 mL with PBS. One mL of cold-saturated ammonium sulfate warmed to room temperature was added to bring the final concentration of ammonium sulfate to 14.3% of saturation. The reaction mixture was then centrifuged for 10 minutes at 2000×g, 25° C. The supernatant was discarded and the precipitate redissolved in 6.0 mL of distilled water. The ammonium sulfate precipitation was repeated for a total of three times and the final pellet dissolved in 2.0 mL of PBS. The polyNIPAAm/MAb solution was then applied to a Sephadex G-25 column to desalt it.

4. Isolation of polyNIPAAm/MAb conjugate by hydroxylapatite chromatography

Figure 2:
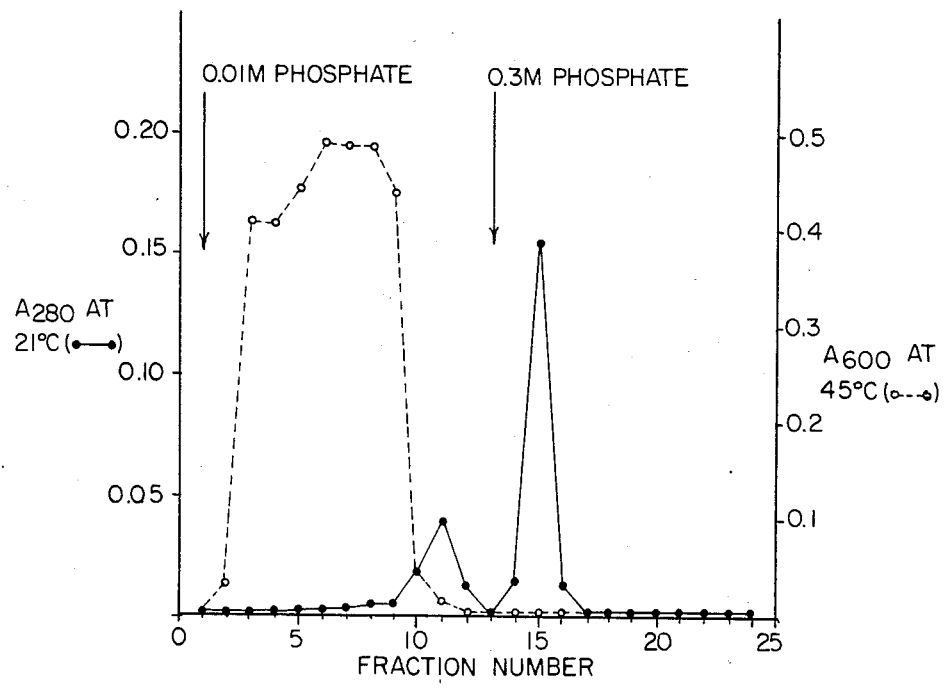
FIG. 2 depicts the elution profile of hydroxylapatite chromatography of MAb(2H1)-polyNIPAAm/-polyNIPAAm mixture.

Partially purified polyNIPAAm/MAb conjugate (1.5 mg Ab) isolated by the $(NH_4)_2SO_4$ precipitation method was dissolved in 2 ml of PBS and then diluted threefold with distilled water. The sample was applied onto a column of hydroxylapatite (1.5 cm×1.0 cm) equilibrated with 0.01M phosphate, pH 6.8. The column was eluted with 0.01M phosphate, pH 6.8, until no more protein and polyNIPAAm was eluted. The elution buffer was then switched to 0.3M phosphate, pH 6.8, to elute the bound polyNIPAAm/MAb conjugate from the hydroxylapatite column. The fractions containing the major protein peak were collected and stored for later use. The elution profile of hydroxylapatite chromatography is shown in FIG. 2, which illustrates that this chromatographic technique further purifies the polyNIPAAm/MAb conjugate by removing excess polyNIPAAm molecules that were co-precipitated in the $(NH_4)_2SO_4$ precipitation method.

Figure 3:
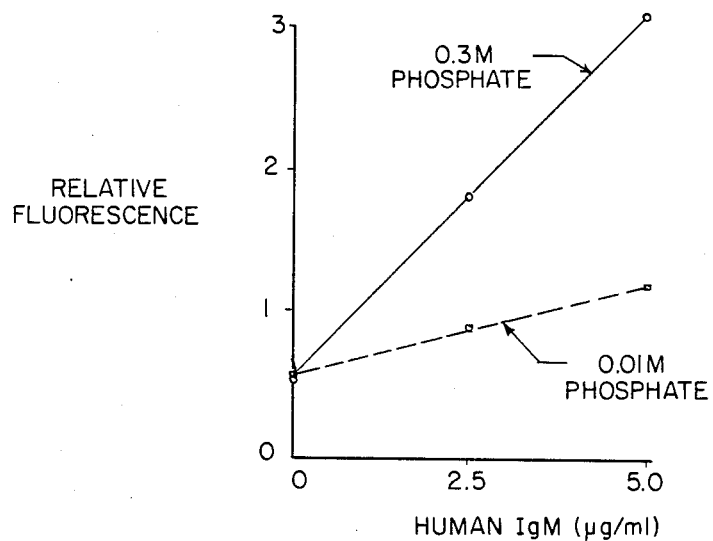
FIG. 3 depicts a pair of standard curves for human IgM in a double antibody-antigen capture assay using protein-polymer conjugate.

The activity of polyNIPAAm/MAb conjugate isolated by this technique in immunoassay was demonstrated using the procedure described in Example IV. Protein fractions eluted at either 0.01M phosphate, pH 6.8, or 0.3M phosphate, pH 6.8, were compared, and the results are shown in FIG. 3. The polyNIPAAm/MAb conjugate eluted at 0.3M phosphate was active in the thermally-induced phase separation immunoassay, whereas the protein eluted at 0.01M phosphate was found to be mostly contaminating protein present in the purified monoclonal antibody.

Figure 4:
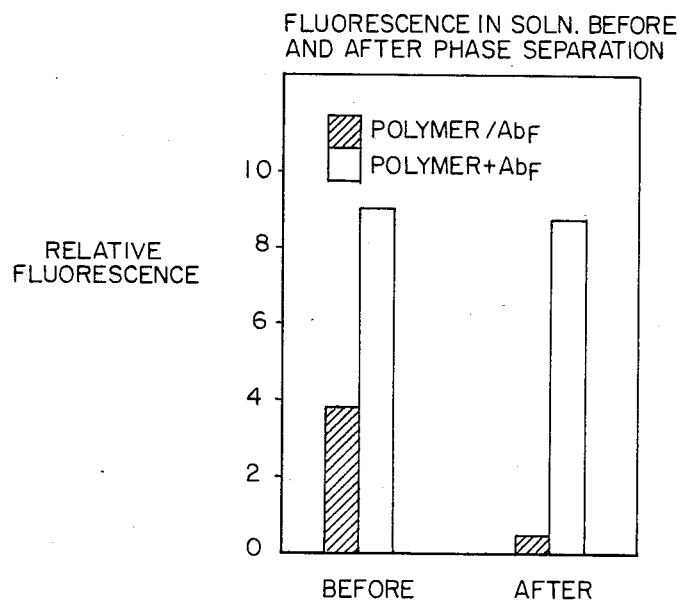
FIG. 4 depicts the percent incorporation of a fluorsceinated monoclonal antibody reactant into a polymer conjugate.

C. Studies on percent incorporation of $McAb_{m,f}$ into polyNIPAAm after a single thermal precipitation $MAb_{m,f}$ was copolymerized with 1% NIPAAm under the same conditions as described in section (IB), except the antibody concentration was reduced to 100 ug/ml and the copolymerization time was increased to 24 hours. The reaction mixture was incubated at 37° C. for 10 minutes and then centrifuged for 5 minutes at 8,000×g at 37° C. The supernatant was withdrawn and the amount of fluorescence remaining in solution determined. The difference in the amount of fluorescence before and after precipitation was expressed as % Ab incorporated into the polymer. As shown in FIG. 4, about 87% of the fluorescence was incorporated into the precipitated polymer.

When the polyNIPAAm was precipitated in the presence of a fluoresceinated bystander antibody, only about 1.7% of the fluorescence was incorporated into the polyNIPPAm precipitate, indicating the nonspecific binding to the polymer is low.

D. Recovery of polyNIPAAm/$MAb_f$ from various assay milieus after serial precipitation One hundred microliters of polyNIPAAm/$MAb_f$ (prepared above) was diluted 1:4 with either PBS, PBS containing 0.05% (w/v) Tween (PBS/Tween), PBS containing 1% BSA (PBS/BSA), or normal human serum (diluted 1:3 in PBS/BSA). The mixtures were incubated for 10 minutes at 37° C. and then centrifuged for 5 minutes at 4,000×g at 37° C. The supernatants were removed and 500 ul of ice-cold PBS was added to each to dissolve the polyNIPAAm/$MAb_f$ precipitate. This cycle was repeated three times. After the final precipitation, the precipitate was redissolved in 500 ul of ice-cold PBS and a 150 ul aliquot was diluted into 1,350 ul of PBS. The fluorescence of this solution was determined and expressed as % fluorescence recovered. The results indicated that inclusion of a non-ionic detergent, BSA, or serum had little or no effect on the precipitability of the polymer conjugate.

Analagous experiments, for which data is not shown, have indicated that the non-ionic detergents Triton X100 Nonidet P40 (NP40) and Tween 20, up to a concentration of 1%, have of no effect on the precipitability of the polymer conjugate. The ionic detergent sodium dodecyl sulphate (SDS), up to a concentration of 0.025%, likewise has no effect, while the detergents deoxycholate (DOC) and sodium cholate have no effect up to a concentration of 1%. Divalent anions (sulfate, carbonate, and phosphate), up to a concentration of 0.25M, have no effect on the precipitability of the conjugate. The divalent cation calcium has no effect up to a concentration of 0.125M, whereas magnesium has no effect up to a concentration of 1M. Monovalent cations, such as lithium and sodium, have no effect at concentrations below 1M; likewise, monovalent anions (chloride, thiocyanate) have no effect up to a concentration of 1M. Other substances which do not appear to effect precipitability of the conjugate include the anticoagulants sodium citrate (up to a concentration of 0.25M), heparin (up to 2500 units/mL), EDTA (up to 0.05M), urea (up to 0.5M), creatinine (up to 0.125M), and polyethylene glycol (up to 6.25%).

EXAMPLE II

Competitive Fluorescence Immunoassay for the Quantitation of Mouse IgG

Mouse IgG standards were prepared in PBS/1% (w/v) BSA to the following concentrations: 0, 0.5, 5.0, and 50.0 ug/mL.

Goat anti-mouse IgG, fluorescently labeled (g$\alpha$-MIg/F), was obtained fro Pel-Freez Biologicals (Rogers, Ark.) and diluted prior to use 1:100 in PBS/BSA.

NIPAAm was conjugated with MAb$_M$ as described in I.A. above, polymerized as in I.B., and purified as in I.B.2. Fifty microliters each of mouse IgG standard, g$\alpha$-MIg/F, and polyNIPAAm/MAb were admixed with 350 uL of PBS/BSA. The resultant mixture was incubated for 30 minutes at room temperature to allow specific binding to occur. The polymer was then precipitated by incubating for 10 minutes at 37° C. The resultant precipitate was pelleted by centrifugation at 4,000×g for 5 minutes at 37° C., the supernatant withdrawn, and the pellet redissolved in 1 mL of ice-cold PBS. This procedure was repeated for a total of two times and the last pellet was redissolved in 200 uL of ice-cold PBS. A 150 uL aliquot of this solution was diluted into 1,350 uL of PBS and the fluorescence determined in a fluorimeter using $\lambda_{ex}$ 494 nm, $\lambda_{em}$ 520 nm.

Figure 5:
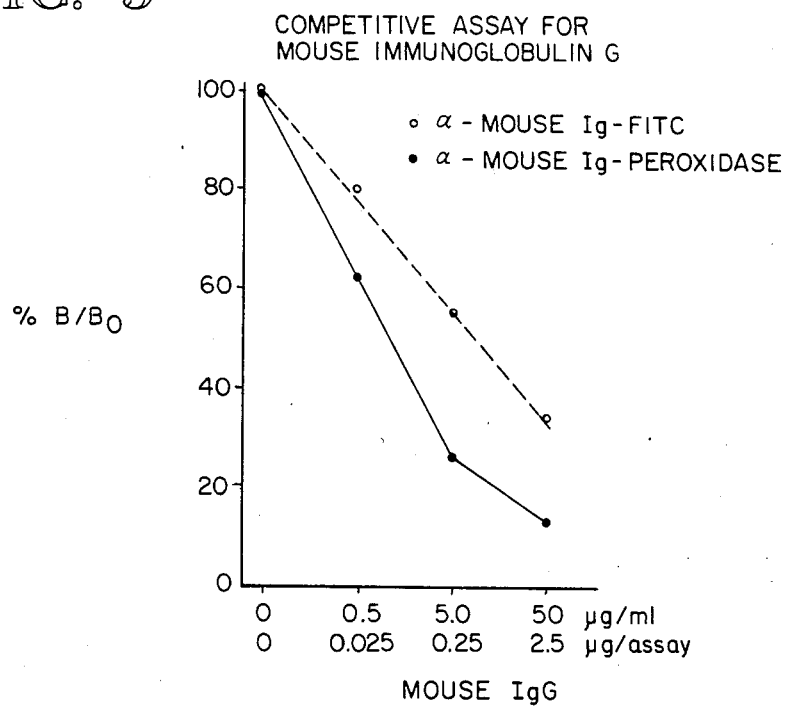
FIG. 5 depicts standard curves for determining the amount of mouse IgG in an unknown sample by a competitive immunoassay.

The resultant standard curve is illustrated in FIG. 5.

EXAMPLE III

Competitive Enzyme Immunoassay for the Quantitation of Mouse IgG

The assay was performed as described in (II) above except that a sheep anti-mouse Ig, labeled with horseradish peroxidase (S$\alpha$mIg/HRP) and diluted 1:1000 in PBS/BSA, was used instead of g$\alpha$mIg/F.

After the second precipitation, the pellet was dissolved in 200 uL of ice-cold PBS and a 25 uL aliquot was transferred to a microtiter well. 100 uL of substrate solution (1 mg OPD/mL in citrate-phosphate buffer, pH 5.0, containing 0.03% H$_2$O$_2$) was added. The reaction mixture was incubated for 15 minutes at room temperature and then the reaction was stopped by the addition of 50 uL 2.5 NH$_2$SO$_4$. Absorbance was determined at 490 nm using a microELISA reader. The resultant standard curve is shown in FIG. 5.

EXAMPLE IV

Antigen Capture Assay for Human IgG (Thermally-Induced Precipitation)

A series of human IgG standards were prepared in PBS/BSA to the following concentrations: 0, 0.05, 0.10, 0.19, 0.375, 0.75 ug/mL.

A polyNIPAAm/monoclonal antibody 2H1 conjugate was prepared as described in Example (I.B.) above. A monoclonal antibody specific for the gamma chain of human IgG, designated 3F6, was labeled with either fluorescein (FITC) or phycoerythrin (PE).

Figure 6:
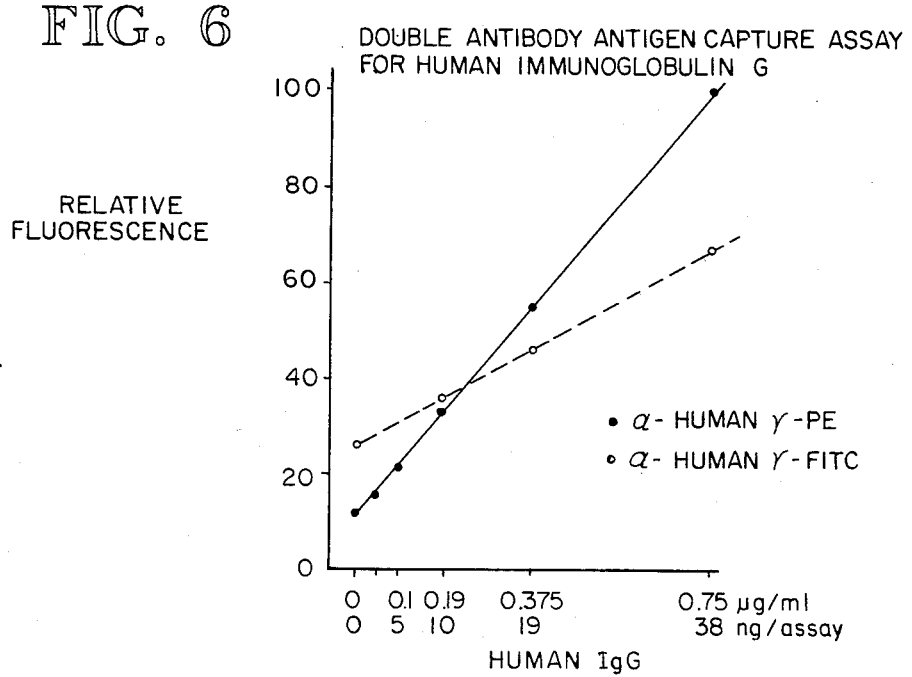
FIG. 6 depicts standard curves for determining the amount of human IgG in an unknown sample by an antigen capture immunoassay.

The assay was performed as follows: To 300 uL of PBS/BSA was added the following reagents: 50 uL of polyNIPAAm/2H1 conjugate (200 ug of antibody per mL in 0.1% polyNIPAAm), 50 uL of 1% polyNIPAAm (as a co-precipitating agent), 50 uL of IgG standard, and 100 uL of either 3F6/FITC (1.5 ug) or 100 uL of 3F6/PE (1 ug.). The reaction mixture was incubated for 60 minutes at room temperature to allow specific binding to occur. The temperature was then raised to 45° C. for ten minutes to precipitate the polymer. The resultant precipitate was pelleted by centrifugation at 4,000×g for 5 minutes at 37° C. The supernatant was withdrawn and the precipitate was redissolved in 1 mL of ice-cold PBS. The temperature was again raised to 45° C. to precipitate the polymer, the resultant precipitate was pelleted by centrifugation, the supernatant withdrawn, and the pellet redissolved in 200 uL of ice-cold PBS. A 150 uL aliquot of the resultant solution was diluted into 1,350 uL of PBS and the fluorescence measured in a fluorimeter ($\lambda_{ex}$ 494 nm, $\lambda_{em}$ 520 nm for fluorescein; $\lambda_{ex}$ 545 nm, $\lambda_{em}$ 575 nm for PE). The resultant standard curves are shown in FIG. 6.

EXAMPLE V

Sandwich Immunoassay for Rabbit Anti-mouse IgG (Thermally-Induced Precipitation)

A series of rabbit anti-mouse IgG standards were prepared by diluting an antiserum 1:20, 1:100, 1:250, 1:500, or 1:12,500 in PBS/BSA. A polyNIPAAm/monoclonal antibody 2H1 conjugate was prepared as described above (100 ug of antibody per mL).

Figure 7:
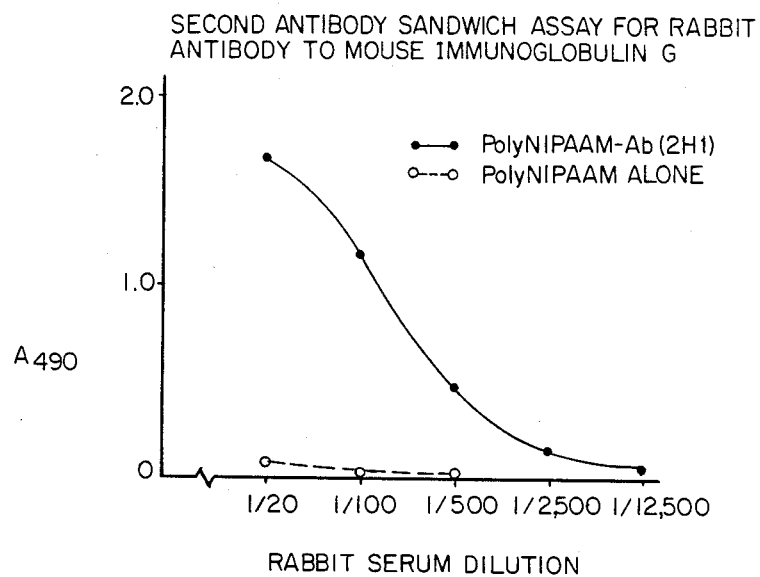
FIG. 7 depicts a standard curve for determining the amount of rabbit anti-mouse IgG in an unknown sample by a sandwich immunoassay.

The assay was performed as follows: To 300 uL of PBS/BSA was added 50 uL of polyNIPAAm/2H1 conjugate, 50 uL of 1% polyNIPAAm (as a co-precipitating agent), and 100 uL of a dilution of rabbit anti-mouse IgG. The reaction mixture was incubated for 30 minutes at room temperature to allow specific binding to occur. The reaction mixture was then diluted to 1 mL by the addition of 500 uL of PBS. The temperature was raised to 37° C. for ten minutes to precipitate the polymer. The resultant precipitate was pelleted by centrifugation for five minutes at 4,000×g at 37° C. The supernatant was withdrawn and the precipitate was redissolved by the addition of 1 mL of ice-cold PBS. The polymer was again precipitated by raising the temperature to 37° C., the precipitate was pelleted by centrifugation, the supernatant withdrawn, and the precipitate dissolved in 100 uL of goat anti-rabbit IgG/HRP (Cappel Laboratories, diluted 1:1000 in PBS/BSA). The reaction volume was brought to 0.5 mL by the addition of 400 uL of PBS/BSA. Incubation was continued for 30 minutes at room temperature, at which time the reaction volume was brought to 1 mL by the addition of 500 uL of PBS. The reaction mixture was incubated at 37° C. for ten minutes to precipitate the polymer. The resultant precipitate was pelleted by centrifugation at 4,000×g for 5 minutes at 37° C., the supernatant was withdrawn and the pellet was redissolved in 1 mL of ice-cold PBS. This cycle was repeated (for a total of two times), the final precipitate was dissolved in 200 uL of ice-cold PBS, and a 15 uL aliquot transferred to a microtiter well containing 50 ul of PBS/BSA. 100 uL of substrate solution prepared as in Example III above was added and the reaction was incubated for ten minutes at room temperature. The reaction was terminated by the addition of 100 uL of 2.5 $NH_2SO_4$. The absorbance of the resultant solution was measured at 490 nm on a microELISA reader. The resultant standard curve is shown in FIG. 7.

EXAMPLE VI

Antigen Capture Assay for Human IgM (Salt-Induced Precipitation)

A series of human IgM standards was prepared in PBS/BSA to the following concentrations: 0, 1.25 ug/mL, 2.5 ug/mL, 5 ug/mL.

A polyNIPAAm/MAb 2H1 conjugate was prepared as described in Example I.B. above. A monoclonal antibody specific for the mu chain of human IgM, designated 2C3, was labeled with fluorescein isothiocyanate (FITC).

Figure 8:
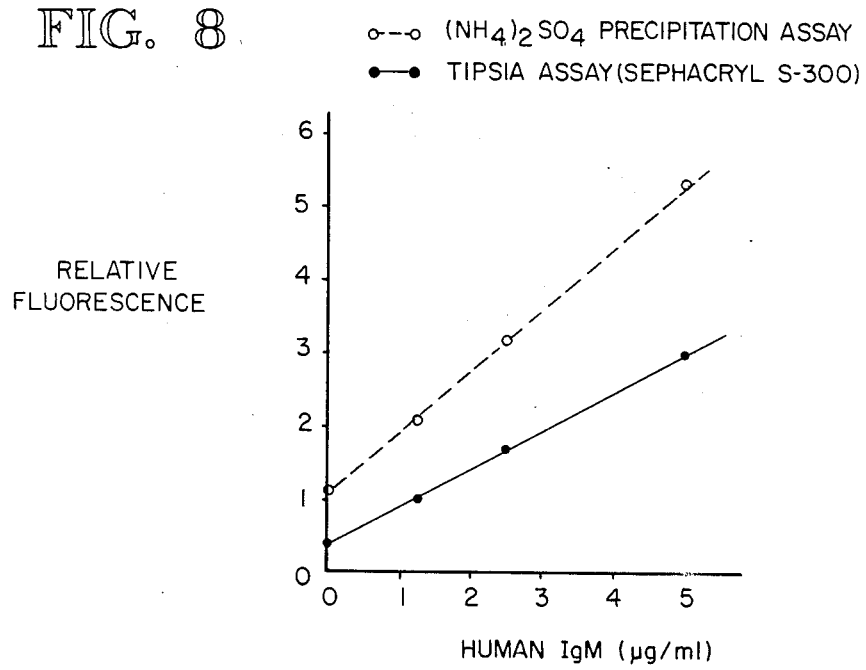
FIG. 8 compares a standard curve for determining human IgM using thermal precipitation and salt-induced precipitation.

The assay was performed as follows: To 150 uL of PBS/BSA was added the following reagents: 12 ul of polyNIPAAm/MAb 2H1 conjugate (4.5 ug antibody per assay), 50 uL of human IgM standard, 100 uL of MAb 2C3/FITC (1.5 ug of antibody per assay), 50 uL of 0.5% polyNIPAAm as carrier, and 50 uL of 0.5% Tween-20. The assay mixture was incubated at 25° C. for 1 hour to allow specific binding to occur. 100 uL of saturated ammonium sulfate was added, and the solution was mixed and centrifuged for 10 minutes at 2000×g at 25° C. The supernatant was discarded and the pellet was redissolved in 800 uL of ice-cold PBS. Precipitation was repeated by the addition of 200 uL of saturated ammonium sulfate followed by centrifugation, removal of the supernatant and redissolution of the pellet in 1 mL of ice-cold PBS. The final solution was added to a cuvette containing 0.5 mL of PBS. Fluorescence was measured in a fluorimeter ($\lambda_{ex}$ 494 nm, $\lambda_{em}$ 520 nm). A typical standard curve in shown in FIG. 8.

EXAMPLE VII

Synthesis and Characterization of Antibody-Conjugated PolyNIPAAm Polyacrylamide (AAm) Copolymer (PANIA)

A. Preparation of acrylamide copolymers of polyNIPAAm

In order to be able to carry out specific binding reactions at temperatures above 31° C. (the LCST of polyNIPAAm), acrylamide copolymers of NIPAAm were synthesized. FIG. 9 shows the lower critical solution temperature (LCST) of these copolymers as a function of increasing concentration of acrylamide and N-substituted acrylamide. For further studies, the 10% acrylamide copolymer of polyNIPAAm was chosen. This copolymer exhibits a LCST of approximately 40°–42° C. and can be phase-separated either by heating above the LCST or by the addition of ammonium sulfate to 20–25% of saturation.

B. Copolymerization of $MAb_m$ with N-isopropylacrylamide (NIPAAm) and Acrylamide (AAm)

To 1.6 mL of 1.2% NIPAAm in PBS, 0.2 mL of 1% acrylamide, 0.2 mL of MAb $2H1_m$ prepared in Example I.A. above (2.5 mg/mL), 0.1 mL of ammonium persulfate (100 mM) and 0.1 mL of TEMED (0.8M) were added. The reaction mixture was incubated at 25° C. for 1 hour, at the end of which time 0.55 mL of saturated ammonium sulfate was added (final concentration 20% of saturation.) The mixture was then centrifuged to precipitate the copolymer/MAb conjugate. After centrifugation for 10 minutes at 2000×g, 25° C., the supernatant was discarded and 1.8 mL of distilled water was added to redissolve the pellet. 0.2 mL of 10X PBS was added, followed by 0.5 mL of saturated ammonium sulfate to re-precipitate the copolymer/MAb conjugate. This cycle of dissolution and precipitation was repeated once more and the final pellet was then dissolved in 1.8 mL of distilled water, followed by the addition of 0.2 mL of 10X PBS. The resultant PANIA/MAb conjugate was stored at 4° C. until further use. This conjugate exhibited an LCST of about 40° C. and remained soluble at temperatures between room temperature and 37° C.

EXAMPLE VIII

Antigen Capture Assay for Human IgM Using an Acrylamide Copolymer of PolyNIPAAm, PANIA (Salt-Induced Precipitation)

A series of human IgM standards was prepared in PBS/BSA to the following concentrations: 1.25, 2.5 and 5 mg/mL.

The polyNIPAAm/polyAAM/MAb conjugate prepared in Example VII.B. above as utilized. A monoclonal antibody specific for the mu chain of human IgM designated 2C3 was labeled with fluorescein isothiocyanate (FITC, $MAb_f$).

The assay was performed as described in Example VII above, using the following volumes of reagents: to 88 uL of 1% PBS/BSA was added 12 ul of PANIA/MAb 2H1 conjugate (240 ug of antibody per mL), 50 uL of antigen standard, 100 uL of $MAb_f$(5 mg per mL), and 50 ul of 0.5% Tween 20. The assay mixture was incubated for 60 minutes at 37° C., at the end of which time 300 uL of PBS was added to bring the total volume up to 600 uL. 200 uL of saturated ammonium sulfate was then added to precipitate the copolymer conjugate. The tubes were centrifuged for 10 minutes at 200×g, 25° C. After centrifugation, the supernatant was discarded and the pellet redissolved in 600 uL of ice-cold PBS. This cycle was repeated for a total of three times. The final pellet was redissolved in 1 mL of ice-cold PBS and added to a cuvette containing 0.5 mL of PBS. Fluorescence was measured in a fluorimeter ($\lambda_{ex}$ 494 nm, $\lambda_{em}$ 520 nm). The resultant standard curve is shown in FIG. 10.

EXAMPLE IX

Synthesis and Characterization of an Antibody-Conjugated, N-n-butyl Acrylamide Copolymer of NIPAAm A. Preparation of N-n-butyl acrylamide copolymers of NIPAAm A series of N-n-butyl acrylamide (NnBA) and N-t-butyl acrylamide (NtBA) copolymers of NIPAAm were synthesized. FIG. 9 shows the lower critical solution temperature (LCST) of these copolymers as a function of increasing concentrations of NnBA or NtBA. Copolymers containing more than 40% NnBA or 70% NtBA, on a monomer basis in the copolymerization mix, did not redissolve at any temperature and provide an upper limit of NnBA or NtBA that is useable under these conditions.

From this data the copolymer resulting from 25% NnBA and 75% NIPAAm was chosen. This copolymer, hereafter referred to as pBNIA, exhibits an LCST of approximately 22°–27° C. and thus can be phase-separated at room temperature.

B. Studies on coprecipitation of copolymers of NIPAAm

Conjugation of Monomer to R-Phycoerythrin

The monomer para-vinyl benzoic acid (PVB) was activated to form the N-hydroxy succinimide ester (NSB) as described in the co-pending patent application U.S. Ser. No. 668,247, herein incorporated by reference.

This monomer was conjugated to R-phycoerythrin (PE). To 9.2 mg of PE in 1.6 ml of 0.29M carbonate buffer pH 9.3 was added 143 ug of NSB in 14.3 ul of tetrahydrofuran (THF). After incubation for 1 hr at 37° C. the reaction mix was purified on a 1.5×5 cm column of Sephasex G-25 which had been equilibrated with PBS. The fractions containing $PE_{PVB}$ were pooled and stored at 4° C.

Copolymerication of $PE_{PVB}$ with NIPAAm and Terpolymerization of $PE_{PVB}$ with Acrylamide and NIPAAm To 2.0 mg of $PE_{PVB}$ in 5.35 ml of PBS were added 594 ul of 1.11% NIPAAm, 330 ul of 0.8M tetramethylethylenediamine (TEMED), pH 7.4 (HCl) and 330 ul of 0.1M ammonium persulfate. After incubation for 2 hrs at room temperature the reaction mixture was purified on a column of Sephacryl S-300 and the fractions containing $PE(A_{565})$ and polyNIPAAm ($A_{600}$ at 45/°C.) were pooled and stored at 4° C.

By a similar procedure $PE_{PVB}$ was terpolymerized with NIPAAm (0.9%) and acrylamide (0.1%).

Coprecipitation studies

To determine whether either of these two fluorescently labeled polymers coprecipitated with pBNIA, each was added to solutions of pBNIA ranging from 0.025 to 0.6%. Aliquots of supernatants from a room temperature centrifugation exhibited the same fluorescence as controls (-pBNIA) both before and after centrifugation, as illustrated in Table 1. Centrifugation at 45° C. then removed more than 70% of the PE-pANIA from solution and more than 80% of the PE-pNIPAAm from solution.

TABLE 1

| Relative Fluorescence Intensity of Supernatant Solutions, Percent of Control | | | | |
|---|---|---|---|---|
| % pBNIA: | 0 | 0.025 | 0.1 | 0.6 |
| +pANIA-PE | 100 | | | |
| Supernate from room temperature centrifugation | 98 | 102 | 104 | 104 |
| Supernate from 45° centrifugation | 20 | 28 | | |
| +pNIPAAm-PE | 100 | | | |
| Supernate from room temperature centrifugation | 100 | | 104 | 103 |
| Supernate from 45° centrifugation | 15 | | 16 | 17 |

These results indicated feasibility of a multianalyte assay using at least two antibodies attached to at least two different polymers. The above experiment demonstrates that despite their similarity in structure and many physical properties, polyNIPAAm and pBNIA can be efficiently separated from each other due to their differences in critical solution temperature. This indicates that other polymers can be separated from each other also, which provides a method for an assay for three or more analytes.

EXAMPLE X

Dual-Analyte Assay for Human IgG and IgM Using an N-butyl Acrylamide Copolymer of NIPAAm Together with the Acrylamide Copolymer pANIA A. Preparation of Reagents Conjugation of Monomer to an Anti-human IgG Monoclonal Antibody The monomer NSB was conjugated to a mouse monoclonal antibody, designated 3F6, specific for the gamma chian of human IgG, by essentially the same procedure as described in Example I.A above. Briefly, to 2.0 mg (0.78 ml) of MAb 3F6, which had been dialyzed overnight against 0.29M sodium carbonate buffer pH 9.3, were added 25.8 ug of NSB in 25.8 ul of THF. After incubation for 1 hr at 37° C. 50 ul was diluted with 1% aqueous phosphoric acid and frozen until analysis by reversed phase high performance liquid chromatography could be performed. The number of monomers per antibody was revealed to be approximately 4. The remainder was passed through a 1.5×5 cm column of Sephadex G-25 which had been equilibrated with phosphate-buffered saline (PBS) pH 7.4. The fractions of the eluate which contained antibody were pooled and stored at −20° C.

Terpolymerization of MAb $3F6_{PVB}$ with N-n-butyl acrylamide (NnBA) and NIPAAm To 0.41 mg (180 ul) of $3F6_{PVB}$ in 0.659 ml of PBS, was added 0.31 ml of 1.11% NnBA, 93 ul of 11.11% NIPAAm, 69 ul of 0.8M TEMED hydrochloride pH 7.4, and 69 ul of 0.1M ammonium persulfate. After incubation for 3 hours at 10° to 18° C., the reaction mix was separated at 4° C. on 1.5×47 cm Sephacryl S-300 column. The fractions of the eluate which contained antibody were pooled and stored at 4° C.

Conjugation of Monomer to an anti-human IgM Monoclonal Antibody

The monomer NSB was also conjugated to a mouse monoclonal antibody specific for the mu chain of human IgG, designated 2C3. To 2.5 mg (0.43 ml) of MAb 2C3, which had been dialyzed overnight against 0.29M sodium carbonate buffer pH 7.3, was added 32.4 ug of NSB in 32.4 ul of THF. After incubation for 1 hr at 37° C., 50 ul was diluted with 1% aqueous phosphoric acid and frozen until analysis by reversed phase high performance liquid chromatography could be performed. This analysis revealed that approximately 4 monomers were conjugated to each antibody. The remainder of the reaction mix was passed through a 1.5×5 cm column of Sephadex G-25 which had been equilibrated with PBS, pH 7.4. The fractions of the eluate which contained antibody were pooled and stored frozen at −20° C.

Terpolymerization of MAb $2C3_{PVB}$ with Acrylamide and NIPAAm

To 0.59 mg of $2C3_{PVB}$ in 1.6 ml of PBS were added 162 ul of 11.11% NIPAAm, 18 ul of 11.11% acrylamide, 100 ul of 0.8M TEMED hydrochloride pH 7.4, and 100 ul of 0.1M ammonium persulfate. After 15 minutes at room temperature the polymerization mix was separated on a 1.5×47 cm Sephacryl S-300 column. The fractions of the eluate which contained antibody were pooled and stored at 4° C. until use.

Other Reagents

A series of human IgG and human IgM standards were prepared in PBS/BSA at the following concentrations: 0, 2, 4, and 6 ug/ml.

A monoclonal antibody specific for the human kappa light chain of human immunoglobulins, designated 2H1, was conjugated to PE.

B. Dual-Analyte Assay

The assay was performed as follows: to 100 ul of 5% BSA in PBS were added 250 ul of 2H1-PE (10 ug), 100 ul of pBNIA/3F6 conjugate (6.8 ug of antibody), 100 ul of 1% pBNIA, 200 ul of human IgG standard, 100 ul of pANIA, and 200 ul of human IgM standard. To one set of tubes an additional 100 ul of 2H1-PE (4 ug) was added after the 30° C. centrifugation. The reaction mixtures were incubated overnight (18 hours) at 4°–8° C. to allow specific binding to occur. The samples were then heated to 29°–30° C. to precipitate the pBNIA and centrifuged at 7–9000×g for 10 minutes at 30° C. The supernatants were withdrawn to other tubes for further processing. The pellets were washed three times with warm (29°–31° C.) PBS (1.5 ul each), and resuspended in 200 ul of ice-cold deionized water.

Figure 11:
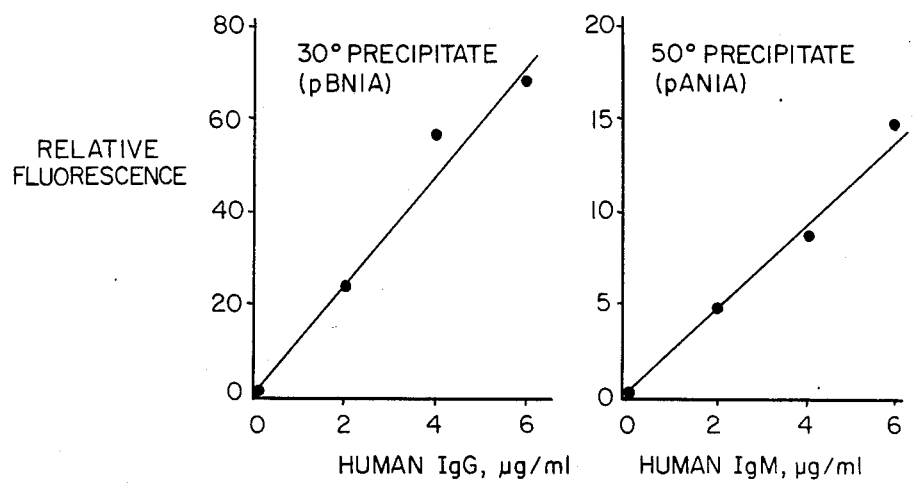
FIG. 11 depicts the selective precipitation and assay of human IgG and IgM at different temperatures.

These solutions were diluted with 1.8 ml of 0.01M phosphate buffer pH 7.4 and measured ona fluorimeter ($\lambda_{ex}$ 540 nm, $\lambda_{em}$ 580 nm). The resultant standard curve is shown in FIG. 11.

The supernatants from above were meanwhile heated to 52° C. for 10 minutes to precipitate the pANIA and centrifuged at 7–9000×g for 10 minutes, also at 52° C. These supernatants were withdrawn, the pellets were washed three times with 1.5 ml of hot (51°–55° C.) PBS, and resuspended with 200 ul of cold PBS. These solutions were measured in a fluorimeter ($\lambda_{ex}$ 540 nm, $\lambda_{em}$ 580 nm) using a flow cell. The resultant standard curve is shown in FIG. 11. This flow cell allowed the inventors to partially take advantage of the volumetric concentration attainable in this assay.

Zero antigen samples were also assayed in the presence of different concentrations of the other antigen and the differences in the fluorescence of the resuspended polymer were seen. These results indicated that the formation of large immune complexes composed of analyte, both antibodies, polymer and phycoerythrin does not alter the background fluorescence in a different polymer.

EXAMPLE XI

Antigen Capture Assay for *Chlamydia trachomatis* Elementary Bodies (Thermally-Induced Precipitation)

In this example, the use of the thermally induced precipitation assay for detecting the presence of a member of the genus Chlamydia is described. Chlamydial elementary bodies, which have an affinity for the polymers disclosed herein, are utilized as analyte within the assay. The reactivity of the polymer with the elementary bodies is also influenced by the nature of the polymer. For instance, the reactivity of the polymer may be influenced by the size of the polymer.

Preparation of Chlamydial Antigen

HeLa 229 cells were grown to confluency in large tissue culture flasks in Eagles minimal essential medium, MEM. Cells were then aspirated and washed two times with MEM. Each flask was then infected with 1.5 ml ($3 \times 10^8$ elementary bodies of *Chlamydia trachomatis* LGV strain L2/434/BU in SPG buffer (75 g sucrose, 52 g $KH_2PO_4$, 1.22 g Na $HPO_4$, and 0.72 glutamate, per liter). Flasks were then incubated at room temperature for 1½ hours with occasional rocking. MEM containing 10% fetal calf serum, 100 µg/ml vancomycin, 100 µg/ml streptomycin, sodium pyruvate and L-glutamine was added to the flask and cells were incubated at 37° C. in 5% $CO_2$ for 3–4 days.

Cells were harvested by scraping them from a flask into 50 ml plastic tubes. Cells were centrifuged at 200×g for five minutes and the resulting supernatant decanted. Cells were resuspended in 20 ml of MEM and respun at 200×g for five minutes. Supernatants were again decanted and cells resuspended in 10 ml of MEM. Cells were then sonicated on ice for two minutes, then centrifuged at 200×g for ten minutes. The supernatant was transferred to a Nalgene centrifuge tube and spun at 20,000×g for 30 minutes to pellet the elementary bodies. The supernatant was aspirated and the elementary bodies resuspended in a final volume of 5 ml SPG and stored at −70° C. Antigen for use in the assays was prepared by fixing samples in 0.02% formalin. Protein was determined by the Bradford method and the number of elementary bodies per ng of protein determined by direct immunofluorescence using FITC-labeled 2Cl as the detection antibody. (Stephens et al., *J. Immunol.* 128: 1083–1089, 1982).

Preparation of 2Cl-HRP Conjugate

Horseradish peroxidase (HRP) was conjugated to monoclonal antibody 2Cl using the following procedure. 10.6 mg of HRP dissolved in 2 ml of distilled water was reacted with 9 mM sodium periodate at room temperature for 20 minutes. The HRP was then desalted on a PD10 column equilibrated with 1 mM sodium acetate in 1M NaCl, pH 4.4. Periodate-oxidized HRP (7.36 mg) was eluted and collected, and 3 mg of the oxidized HRP was then mixed with 2 mg of 2Cl antibody (2 mg/ml) in 0.1M sodium carbonate/1.0M sodium chloride, pH 9.3 (final) to achieve a molar ratio of oxidized HRP to antibody of 6:1. The mixture was incubated for 17 minutes at room temperature, then sodium borohydride (84 ul of 4 mg/ml in distilled water) was added and the mixture incubated for an additional two hours on ice. An equal volume of saturated cold ammonium sulfate solution was then added, vortexed and allowed to stand chilled on ice for 30 minutes. The solution was centrifuged for 20 minutes at 20,000×g and the supernatant removed, and the pellet then washed twice with cold 50% saturated ammonium sulfate. The resulting conjugate was the resuspended in PBS and dialyzed, then mixed with 50% glycerol and stored at −20° C.

Antibody Capture System

In this assay format, two monoclonal antibodies specific for components of the chlamydial elementary bodies were utilized. Antibody IH11 (Stephens et al., *J. Immunol.* 128: 1083–1089, 1982) is specific for the lipopolysaccharide of the elementary bodies, and is coupled to poly-N-isopropylacrylamide as described in Example I.B. Antibody 2Cl is specific for a 39.5 Kd outer membrane protein of *Chlamydia trachomatis* and is coupled to horseradish peroxidase, as described above.

Figure 12:
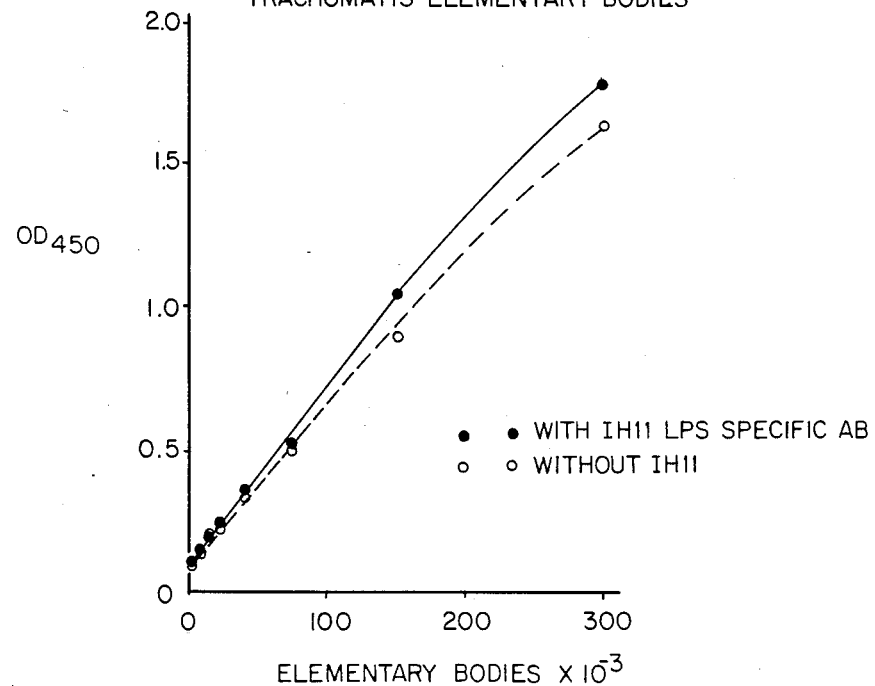
FIG. 12 depicts a standard curve for detection of *C. trachomatis* elementary bodies.

The antibody capture assay was performed in a final volume of 0.5 ml, and consisted of the following components: 1 µg of IH11 coupled to poly-N-isopropylacrylamide (purified on an S300 sephadex column), 0.1% (w/v) poly-N-isopropylacrylamide as carrier and 50 ul of a solution of 20 ng of 2Cl conjugated to HRP in 10% glycerol w/v, 5% v/v mouse ascitic fluid, 1% human serum albumin and 0.02% Tween 20. The assay mix also contained a 0.4% (w/v) final concentration of BSA and 200 ul of antigen (Chlamydia elementary bodies) diluted in a specimen diluent containing citrated nonfat dry milk (2.5% w/v). The reaction mix was incubated for 20 minutes at room temperature then heated for 10 minutes at 45° C. to precipitate the polymer. Following centrifugation at 7000×g for 10 minutes, the supernatant was removed and the diffuse pellet washed twice with hot (45° C.) PBS. The pellet was then suspended in 100 ul of substrate containing 3, $3^1$, 5, $5^1$ tetramethylbenzidine and hydrogen peroxide, and allowed to incubate for 20 minutes at room temperature. The reaction was then stopped with 200 ul of 3N HCl and the optical density measured at 450 nm in a microtiter plate. The reactivity of the elementary bodies in this assay is shown in FIG. 12.

Polymer Capture System

It was also discovered that Chlamydial elementary bodies bind directly to the poly-N-isopropylacrylamide or other similar water soluble, thermally-reversible precipitating polymers. An assay system using this format utilized the same components and conditions as described for the antibody capture assay except that antibody IH11 conjugated to poly-N-isopropylacrylamide was omitted and 10 ng of the 2cl-HRP conjugate was used. The reactivity of the elementary bodies in this assay format is also demonstrated in FIG. 12.

Other polymers of N-isopropylacrylamide have also been shown to act as a capture polymer system, but with differing efficiencies, which has been found to be related, at least in part, to the size of the polymer. As shown in FIG. 13, the reactivity of polymers of different molecular weights give different responses at varying concentrations in the assay. The polymers were prepared in benzene, benzene: tetrahydrofuran (9:1), and tetrahydrofuran as described below. The polymers were assayed at concentrations of 0.2, 0.1, 0.05, 0.025, and 0.0125 percent w/v in this system.

Anhydrous co-polymerization in THF at NIPAAm ratio of 20 to 1 (AT-poly 1)

The conditions for co-polymerization were analogous to those described by Pollack et al. (J. Am. Chem. Soc. 102: 6324-6336, 1980). A 100-ml two-necked round-bottomed flask, fitted with a reflux condenser, thermometer, and nitrogen inlet controlled by a Firestone valve was charged with N-isopropylacrylamide (5 g, 44 L mM, Kodak #10982), N-acryloxysuccinimide (prepared by the method of Pollack et al., J. Am. Chem. Soc. 102: 6324-6336, 1980) (0.372 g, 2.2 mM), azobis (isobutyronitrile) (0.021 g, 0.13 mM, Polysciences #0117), and THF (50 ml, pretreated to control peroxide contamination-deperoxidation by the procesure of D. R. Burfield, (J. Org. Chem. 47: 3821-3824, 1982))). The mixture was stirred, degassed, heated to 50° C. internal temperature, maintained under positive nitrogen pressure for 24 hours, and allowed to cool to room temperature. The solution was filtered through a 0.45M teflon memberane. The filtrate volume was reduced to 50% by rotary evaporation and ethyl ether (100 ml, anhydrous) was added to precipitate the polymer. The product was collected by filtration, washed thoroughly with ethyl ether, and dried (40°-45° C.) under vacuum to yield 4.7 g. The inventors have also synthesized co-polymers.

Anhydrous co-polymerization in benzene

The polymerization procedure followed in this example was the same as that described above, except for the isolation procedure which was slightly modified as follows. After the reaction, the benzene solvent was removed and replaced with 50 ml of tetrahydrofuran (THF). The mixture was stirred at room temperature until all solids had dissolved, while positive nitrogen pressure was maintained. This solution was filtered through glass wool and the filtrate was added to 250 ml of ethyl ether with vigorous mixing to precipitate the polymer. The solid was then isolated as described above. The inventors have also synthesized co-polymers at NIPAAM to NASI ratios of 20:1 1 (AB-poly 1), 40:1 (AB-poly 2), 80:1 (AB-poly 3) and NIPAAm homopolymer (AB-poly 4).

Anhydrous homopolymerization inthe mixture of benzene and THF

The polymerization and isolation procedures followed in this example were the same as those set forth above. However, the solvent used in the polymerization reactions was a mixed solvent consisting of benzene and THF. The benzene/THF ratios used herein were 1/3, 3/1, 9/1, and 99/1. Sephacryl S-400 gel permeation chromatographic profiles of each polyNIPAAM homopolymer were prepared. The present invention provides a method for preparing the polymer-size of one's choice by simply changing the ratio of benzene to THF in the polymerization reaction solvent.

From the foregoing, it will be appreciated that, although specific embodiments of the invention have been described herein for purposes of illustration, various modifications may be made without deviating from the spirit and scope of the invention. Accordingly, the invention is not to be limited except as by the appended claims.

We claim:

1. A method for determining the presence and/or concentration of an analyte in a biological fluid sample, comprising:

conjugating a first reactant which is capable of specifically binding with said analyte to a temperature-sensitive polymer to form a polymer/reactant conjugate;

conjugating a second reactant which is capable of specifically binding with said analyte to a reporter to form a reporter/reactant conjugate;

admixing in solution said polymer/reactant, reporter/reactant and said biological fluid sample suspected of containing said analyte at a temperature other than that at which said polymer will precipitate such that specific binding occurs between said first and second reactants and said analyte, thereby forming a ternary complex;

adjusting the salt concentration of the admixed polymer/reactant, reporter/reactant, and analyte containing sample solution to a concentration sufficient to alter the critical solution temperature of the polymer, such that said complex precipitates from the solution; and measuring the amount of reporter activity in the precipitated complex or in the solution and therefrom determining the presence and/or concentration of said analyte.

2. The method of claim 1 including, after the step of adjusting, separating the precipitated complex from the solution.

3. The method of claim 1 including, after the step of conjugating said first reactant to said polymer, purifying said polymer/reactant conjugate.

4. The method of claim 1 wherein said polymer is characterized by a lower critical solution temperature.

5. The method of claim 2 including, after the step of separating said precipitated complex from said solution, redissolving the precipitated complex in a substantially smaller volume than the original solution volume.

6. The method of claim 1 wherein said analyte is capable of simultaneously reacting with said first and second reactants and is one selected from the group consisting of drugs, vitamins, hormones, proteins, metabolites, cells, viruses, and microorganisms.

7. The method of claim 1 wherein said first and second reactants are selected from the group consisting of antibodies, antigens, lectins, receptors, transport proteins and non-immunoglobulin antibody-binding proteins.

8. The method of claim 1 wherein the salt is selected from the group consisting of ammonium sulfate, sodium sulfate, sodium carbonate, potassium carbonate, and sodium phosphate.

9. The method of claim 1 wherein the salt is ammonium sulfate.

10. The method of claim 1 wherein said reporter is one selected from the group consisting of enzymes, fluorophores, radioisotopes, luminescers and dye particles.

11. The method of claim 1 wherein said polymer is poly-N-isopropylacrylamide.

12. The method of claim 1 wherein said polymer is a copolymer formed from monomers selected to achieve a desired critical solution temperature.

13. The method of claim 12 wherein said copolymer is formed from N-isopropylacrylamide monomers copolymerized with acrylamide monomers.

14. The method of claim 12 wherein said copolymer is formed from N-isopropylacrylamide monomers copolymerized with monomers selected from the group consisting of acrylamide monomers, N-ethyl acrylamide monomers, N-methyl acrylamide monomers, and N-isopropyl acrylamide monomers.

15. The method of claim 1 wherein said first reactant is conjugated to a monomer and subsequently copolymerized with additional monomers to yield a temperature-sensitive copolymer.

16. The method of claim 15 wherein said first reactant is conjugated to the N-hydroxysuccinimide ester of acrylic acid and the resultant monomerized reactant copolymerized with a monomer selected from the group consisting of acrylamide monomers, N-isopropyl acrylamide monomers, N-ethyl acrylamide monomers, and N-methyl acrylamide monomers.

17. The method of claim 15 wherein said first reactant is conjugated to the N-hydroxysuccinimide ester of vinyl benzoate and the resultant monomerized reactant copolymerized with a monomer selected from the group consisting of acrylamide monomers, N-isopropyl acrylamide monomers, N-ethyl acrylamide monomers and N-methyl acrylamide monomers.

18. A method for conducting multiple analyses on a single biological fluid sample suspected of containing one or more analytes, comprising:

conjugating a plurality of selected first reactants, each of said first reactants being capable of specifically binding with one of said analytes, to a plurality of temperature-sensitive polymers, each of said first reactants being conjugated to a polymer having a critical solution temperature, thereby forming multiple polymer/reactant conjugates;

conjugating a plurality of selected second reactants, each of said second reactants being capable of specifically binding with one of said analytes, to a reporter to form multiple reporter/reactant conjugates;

admixing in solution said multiple polymer/reactant, multiple reporter/reactant, and said biological fluid sample suspected of containing one or more analytes at a temperature other than that at which any of said polymers will precipitate such that specific binding occurs between said reactants and said analytes, thereby forming a plurality of ternary complexes;

adjusting the salt concentration of the admixed polymer/reactant, reporter/reactant, and analyte sample containing solution incrementally to alter the critical solution temperature of the polymers such that the complex precipitated with each concentration increment can be separated from said solution prior to the precipitation of a complex with a different critical solution temperature; and measuring the amount of the respective reporter activity in each of the precipitated complexes or in the solution and therefrom determining the presence and/or concentration of each of said analytes.

19. The method of claim 18 including, after the step of adjusting the salt concentration of the solution, separating each of said complexes from the solution as the concentration is altered incrementally.

20. The method of claim 18 including, after the step of conjugating said first reactants to said polymers, purifying said polymer/reactant conjugates.

21. The method of claim 18 wherein said polymer is characterized by a lower critical solution temperature.

22. The method of claim 19 including, after the step of separating said precipitated complexes from said solution, redissolving the precipitated complexes in a substantially smaller volume than the original solution volume.

23. The method of claim 18 wherein the salt is selected from the group consisting of ammonium sulfate, sodium sulfate, sodium carbonate, potassium carbonate, and sodium phosphate.

24. The method of claim 18 wherein the salt is ammonium sulfate.

25. The method of claim 18 wherein said analyte is capable of simultaneously reacting with said first and second reactants and is one selected from the group consisting of drugs, vitamins, hormones, proteins, metabolites, cells, viruses, and microorganisms.

26. The method of claim 18 wherein said first and second reactants are selected from the group consisting of antibodies, antigens, lectins, receptors, transport proteins, and non-immunoglobulin antibody-binding proteins.

27. The method of claim 18 wherein said reporter is one selected from the group consisting of enzymes, fluorophores, radioisotopes, luminescers and dye particles.

28. The method of claim 18 wherein said polymer is poly-N-isopropylacrylamide.

29. The method of claim 18 wherein said polymer is a copolymer formed from monomers selected to achieve a desired critical solution temperature.

30. The method of claim 29 wherein said copolymer is formed from N-isopropylacrylamide monomers copolymerized with acrylamide monomers.

31. The method of claim 29 wherein said copolymer is formed from N-isopropylacrylamide monomers copolymerized with monomers selected from the group consisting of acrylamide monomers, N-ethyl acrylamide monomers, N-methyl acrylamide monomers, and N-isopropyl acrylamide monomers.

32. The method of claim 18 wherein said first reactant is conjugated to a monomer and subsequently copolymerized with additional monomers to yield a temperature-sensitive copolymer.

33. The method of claim 32 wherein said first reactant is conjugated to the N-hydroxysuccinimide ester of acrylic acid and the resultant monomerized reactant copolymerized with a monomer selected from the group consisting of acrylamide monomers, N-isopropyl acrylamide monomers, N-ethyl acrylamide monomers, and N-methyl acrylamide monomers.

34. The method of claim 32 wherein said first reactant is conjugated to the N-hydroxysuccinimide ester of vinyl benzoate and the resultant monomerized reactant copolymerized with a monomer selected from the group consisting of acrylamide monomers, N-isopropylacrylamide monomers, N-ethyl acrylamide monomers, and N-methyl acrylamide monomers.

35. A method for determining the presence and/or concentration of an analyte in a biological fluid sample, comprising:
   conjugating a first reactant which is capable of specifically binding with said analyte to a monomer to form a monomer/reactant conjugate;
   copolymerizing said monomer/reactant conjugate with additional monomers to yield a temperature-sensitive copolymer/reactant;
   conjugating a second reactant which is capable of specifically binding with said analyte to a reporter to form a reporter/reactant conjugate;
   admixing in solution said copolymer/reactant, reporter/reactant, and said biological fluid sample suspected of containing said analyte at a temperature other than that at which said copolymer will precipitate such that specific binding occurs between said first and second reactants and said analyte, thereby forming a ternary complex;
   adjusting the salt concentration of the admixed copolymer/reactant, reporter/reactant, and analyte containing sample solution to a salt concentration sufficient to alter the critical solution temperature of the copolymer, such that said complex precipitates from the solution; and
   measuring the amount of reporter activity in the precipitated complex or in the solution and therefrom determining the presence and/or concentration of said analyte.

36. The method of claim 35 including, after the step of adjusting, separating the precipitated complex from the solution.

37. The method of claim 36 including, after the step of separating said precipitated complex from said solution, redissolving the precipitated complex in a substantially smaller volume that the original solution volume.

38. The method of claim 35 wherein said analyte is capable of simultaneously reacting with said first and second reactants and is one selected from the group consisting of drugs, vitamins, hormones, proteins, metabolites, cells, viruses, and microorganisms.

39. The method of claim 35 wherein said first and second reactants are selected from the group consisting of antibodies, antigens, lectins, receptors, transport proteins and non-immunoglobulin antibody-binding proteins.

40. The method of claim 35 wherein said reporter is one selected from the group consisting of enzymes, fluorophores, radioisotopes, luminescers and dye particles.

41. The method of claim 35 wherein the salt is selected from the group consisting of ammonium sulfate, sodium sulfate, sodium carbonate, potassium carbonate, and sodium phosphate.

42. The method of claim 35 wherein the salt is ammonium sulfate.

43. The method of claim 35 wherein said polymer is one characterized by a lower critical solution temperature.

44. The method of claim 35 wherein said first reactant is conjugated to the N-hydroxysuccinimide ester of acrylic acid and the resultant monomerized reactant copolymerized with a monomer selected from the group consisting of acrylamide monomers, N-isopropylacrylamide monomers, N-ethyl acrylamide monomers, and N-methyl acrylamide monomers.

45. The method of claim 35 wherein said first reactant is conjugated to the N-hydroxysuccinimie ester of vinyl benzoate and the resultant monomerized reactant copolymerized with a monomer selected from the group consisting of acrylamide monomers, N-isopropylacrylamide monomers, N-ethyl acrylamide monomers, and N-methyl acrylamide monomers.

46. A method for conducting multiple analyses on a single biological fluid sample suspected of containing one or more analytes, comprising:
   conjugating a plurality of selected first reactants, each of said first reactants being capable of specifically binding with one of said analytes to a plurality of temperature-sensitive polymers, each of said first reactants being conjugated to a polymer having a critical solution temperature, thereby forming multiple polymer/reactant conjugates;
   conjugating a plurality of selected second reactants, each of said second reactants being capable of specifically binding with one of said analytes, to one or more reporters to form multiple reporter/reactant conjugates;
   admixing in solution said multiple polymer/reactant, multiple reporter/reactant, and said biological fluid sample suspected of containing one or more analytes at a temperature other than that at which any of said polymers will precipitate such that specific binding occurs between said reactants and said analytes, thereby forming a plurality of ternary complexes;
   altering the temperature of the admixed polymer/reactant, reporter/reactant, and analyte sample containing solution incrementally such that the complex precipitated with each temperature increment can be separated from said solution prior to the precipitation of a complex with a different critical solution temperature; and
   measuring the amount of the respective reporter activity in each of the precipitated complexes or in the solution and therefrom determining the presence and/or concentration of each of said analytes.

47. The method of claim 46 including, after the step of altering the temperature of the solution, separating each of said complexes from the solution as the temperature is altered incrementally.

48. The method of claim 46 including, after the step of conjugating said first reactants to said polymers, purifying said polymer/reactant conjugates.

49. The method of claim 47 including, after the step of separating said precipitated complexes from said solution, redissolving the precipitated complexes in a substantially smaller volume than the original solution volume.

50. The method of claim 46 wherein said analyte is capable of simultaneously reacting with said first and second reactants and is one selected from the group consisting of drugs, vitamins, hormones, proteins, metabolites, cells, viruses, and microorganisms.

51. The method of claim 46 wherein said first and second reactants are selected from the group consisting of antibodies, antigens, lectins, receptors, transport proteins, and non-immunoglobulin antibody-binding proteins.

52. The method of claim 46 wherein said reporter is one selected from the group consisting of enzymes, fluorophores, radioisotopes, luminescers and dye particles.

53. The method of claim 46 wherein said polymer is one characterized by a lower critical solution temperature, thereby precipitating upon heating said solution above said temperature.

54. The method of claim 53 wherein said polymer is one selected from the group consisting of polyvinyl methyether, polyvinylmethyl oxazolidone, polymethacrylic acid, poly-N-isopropylacrylamide, hydroxypropyl cellulose and methyl cellulose.

55. The method of claim 53 wherein said polymer is poly-N-isopropylacrylamide.

56. The method of claim 46 wherein said polymer is one characterized by an upper critical solution temperature, thereby precipitating upon cooling said solution below said temperature.

57. The method of claim 56 wherein said polymer is one selected from the group consisting of polyethylene glycol, polyacrylic acid, polymethacrylamide and polyvinyl alcohol.

58. The method of claim 53 or 56 wherein said polymer is a copolymer formed from monomers selected to achieve a desired critical solution temperature.

59. The method of claim 58 wherein said copolymer is formed from N-isopropylacrylamide monomers copolymerized with acrylamide monomers.

60. The method of claim 58 wherein said copolymer is formed from N-isopropylacrylamide monomers copolymerized with monomers selected from the group consisting of acrylamide monomers, N-ethyl acrylamide monomers, N-methyl acrylamide monomers, and N-isopropyl acrylamide monomers.

61. The method of claim 46 wherein said first reactant is conjugated to a monomer and subsequently copolymerized with additional monomers to yield a temperature-sensitive copolymer.

62. The method of claim 61 wherein said first reactant is conjugated to the N-hydroxysuccinimide ester of acrylic acid and the resultant monomerized reactant copolymerized with a monomer selected from the group consisting of acrylamide monomers, N-isopropyl acrylamide monomers, N-ethyl acrylamide monomers, and N-methyl acrylamide monomers.

63. The method of claim 61 wherein said first reactant is conjugated to the N-hydroxysuccinimide ester of vinyl benzoate and the resultant monomerized reactant copolymerized a monomer selected from the group consisting of with acrylamide monomers, N-isopropyl acrylamide monomers, N-ethyl acrylamide monomers, and N-methyl acrylamide monomers.

64. A method for determining the presence and/or concentration of a member of the genus Chlamydia in a biological fluid sample, comprising:
   providing a temperature-sensitive polymer characterized by a critical solution temperature that is capable of binding to the elementary bodies of a member of the genus Chlamydia;
   conjugating a first reactant which is capable of specifically binding with said member to a reporter to form a reporter/reactant conjugate;

admixing in solution said polymer, reporter/reactant and said biological fluid sample suspected of containing said member at a temperature other than that at which said polymer will precipitate such that binding occurs between said polymer and said first reactant and said member, thereby forming a ternary complex;

incubating the admixed polymer, reporter/reactant, and member containing sample solution at a temperature sufficient to cause said complex to precipitate from the solution; and measuring the amount of reporter activity in the precipitated complex or in the solution and therefrom determining the presence and/or concentration of said member of the genus Chlamydia.

65. The method of claim 64 wherein said member of the genus Chlamydia is *Chlamydia trachomatis.*

66. The method of claim 64 wherein said polymer is poly-N-isopropylacrylamide.

67. The method of claim 64 including, after the step of incubating, separating the precipitated complex from the solution.

68. The method of claim 64 wherein said reporter is selected from the group consisting of enzymes, fluorophores, radioisotopes, luminescers, and dye particles.

69. The method of claim 64 wherein said first reactant is an antibody.

70. A method for conducting multiple analyses on a single biological fluid sample suspected of containing one or more analytes, comprising:

conjugating a plurality of selected first reactants, each of said first reactants being capable of specifically binding with one of said analytes, to a plurality of temperature-sensitive polymers, each of said first reactants being conjugated to a polymer having a critical solution temperature, thereby forming multiple polymer/reactant conjugates;

conjugating a plurality of selected second reactants, each of said second reactants being capable of specifically binding with one of said analytes, to one or more reporters to form multiple reporter/reactant conjugates;

admixing in solution said multiple polymer/reactant, multiple reporter/reactant, and said biological fluid sample suspected of containing one or more analytes at a temperature other than that at which any of said polymers will precipitate such that specific binding occurs between said reactants and said analytes, thereby forming a plurality of ternary complexes;

selectively modifying the conditions of the admixed polymer/reactant, reporter/reactant, and analyte sample containing solution by incubating the admixed solution and adjusting the salt concentration of the admixed solution at least once to alter the critical solution temperature of the polymers such that the complex precipitated with each temperature or concentration increment can be separated from said solution prior to the precipitation of a complex with a different critical solution temperature; and measuring the amount of the respective reporter activity in each of the precipitated complexes or in the solution and therefrom determining the presence and/or concentration of each of said analytes.

71. The method of claim 70 including, after the step of selectively modifying the conditions, separating each of said complexes from the solution as the temperature or concentration is altered incrementally.

72. The method of claim 70 including, after the step of conjugating said first reactants to said polymers, purifying said polymer/reactant conjugates.

73. The method of claim 70 wherein said polymer is one characterized by a lower critical solution temperature.

74. The method of claim 71 including, after the step of separating said precipitated complexes from said solution, redissolving the precipitated complexes in a substantially smaller volume than the original solution volume.

75. The method of claim 70 wherein the salt is selected from the group consisting of ammonium sulfate, sodium sulfate, sodium carbonate, potassium carbonate, and sodium phosphate.

76. The method of claim 70 wherein the salt is ammonium sulfate.

77. The method of claim 70 wherein said analyte is capable of simultaneously reacting with said first and second reactants and is one selected from the group consisting of drugs, vitamins, hormones, proteins, metabolites, cells, viruses, and microorganisms.

78. The method of claim 70 wherein said first and second reactants are selected from the group consisting of antibodies, antigens, lectins, receptors, transport proteins, and non-immunoglobulin antibody-binding proteins.

79. The method of claim 70 wherein said reporter is one selected from the group consisting of enzymes, fluorophores, radioisotopes, luminescers and dye particles.

80. The method of claim 70 wherein said polymer is poly-N-isopropylacrylamide.

81. The method of claim 70 wherein said polymer is a copolymer formed from monomers selected to achieve a desired critical solution temperature.

82. The method of claim 70 wherein said first reactant is conjugated to a monomer and subsequently copolymerized with additional monomers to yield a temperature-sensitive copolymer.

83. A method for determining the presence and/or concentration of an analyte in a biological fluid sample, comprising:
conjugating a first reactant which is capable of specifically binding with said analyte to a temperature-sensitive polymer characterized by a critical solution temperature to form a polymer/reactant conjugate;
conjugating a second reactant which is capable of specifically binding with said analyte to a reporter to form a reporter/reactant conjugate;
admixing in solution said polymer/reactant, reporter/reactant and said biological fluid sample suspected of containing said analyte at a temperature other than that at which said polymer will precipitate such that specific binding occurs between said first and second reactants and said analyte, thereby forming a ternary complex;
incubating the admixed polymer/reactant, reporter/reactant, and analyte containing sample solution at a temperature sufficient to cause said complex to precipitate from the solution; and
measuring the amount of reporter activity in the precipitated complex or in the solution and therefrom determining the presence and/or concentration of said analyte.

84. The method of claim 83 including, after the step of incubating, separating the precipitated complex from the solution.

85. The method of claim 83 including, after the step of conjugating said first reactant to said polymer, purifying said polymer/reactant conjugate.

86. The method of claim 85 wherein said polymer/reactant conjugate is purified by gel-permeation chromatography or serial precipitation.

87. The method of claim 84 including, after the step of separating said precipitated complex from said solution, redissolving the precipitated complex in a substantially smaller volume than the original solution volume.

88. The method of claim 83 wherein said analyte is capable of simultaneously reacting with said first and second reactants and is one selected from the group consisting of drugs, vitamins, hormones, proteins, metabolites, cells, viruses, and microorganisms.

89. The method of claim 83 wherein said first and second reactants are selected from the group consisting of antibodies, antigens, lectins, receptors, transport proteins and non-immunoglobulin antibody-binding proteins.

90. The method of claim 89 wherein said non-immunoglobulin antibody-binding protein is protein A.

91. The method of claim 83 wherein said reporter is one selected from the group consisting of enzymes, fluorophores, radioisotopes, luminescers and dye particles.

92. The method of claim 83 wherein said reporter is a fluorophore selected from the group consisting of fluorescein, rhodamine, phycoerythrin, phycocyanin, and Nile blue.

93. The method of claim 83 wherein said reporter is an enzyme selected from the group consisting of horseradish peroxidase, $\beta$-galactosidase and alkaline phosphatase.

94. The method of claim 83 wherein said polymer is one selected from the group consisting of polyvinyl methylether, polyvinylmethyl oxazolidone, polymethacrylic acid, poly-N-isopropylacrylamide, hydroxypropyl cellulose and methyl cellulose.

95. The method of claim 83 wherein said polymer is poly-N-isopropylacrylamide.

96. The method of claim 83 wherein said polymer is a copolymer formed from monomers selected to achieve a desired critical solution temperature.

97. The method of claim 96 wherein said copolymer is formed from N-isopropylacrylamide monomers copolymerized with acrylamide monomers.

98. The method of claim 83 wherein said first reactant is conjugated to a monomer and subsequently copolymerized with additional monomers to yield a temperature-sensitive copolymer characterized by a lower critical solution temperature.

99. The method of claim 98 wherein said first reactant is conjugated to the N-hydroxysuccinimide ester of acrylic acid and the resultant monomerized reactant copolymerized with N-isopropylacrylamide.

100. The method of claim 98 wherein said first reactant is conjugated to the N-hydroxysuccinimide ester of vinyl benzoate and the resultant monomerized reactant copolymerized with N-isopropylacrylamide.

101. The method of claim 83 wherein said polymer is one selected from the group consisting of polyethylene glycol, polyacrylic acid, polymethacrylamide and polyvinyl alcohol.

102. The method of claim 83 wherein said polymer is a copolymer formed from monomers selected to achieve a desired critical solution temperature.

103. A method for determining the presence and/or concentration of an analyte in a biological fluid sample, comprising:
 conjugating a first reactant which is capable of specifically binding with said analyte to a monomer to form a monomer/reactant conjugate;
 copolymerizing said monomer/reactant conjugate with additional monomers to yield a temperature-sensitive copolymer/reactant;
 conjugating a second reactant which is capable of specifically binding with said analyte to a reporter to form a reporter/reactant conjugate;
 admixing in solution said copolymer/reactant, reporter/reactant, and said biological fluid sample suspected of containing said analyte at a temperature other than that at which said copolymer will precipitate such that specific binding occurs between said first and second reactants and said analyte, thereby forming a ternary complex;
 incubating the admixed copolymer/reactant, reporter/reactant, and analyte containing sample solution at a temperature sufficient to cause said complex to precipitate from the solution; and
 measuring the amount of reporter activity in the precipitated complex or in the solution and therefrom determining the presence and/or concentration of said analyte.

104. The method of claim 103 wherein said polymer is one characterized by a lower critical solution temperature, thereby precipitating upon heating said solution above said temperature.

105. The method of claim 103 wherein said polymer is one characterized by an upper critical solution temperature, thereby precipitating upon cooling said solution below said temperature.

106. The method of claim 103 wherein said first reactant is conjugated to the N-hydroxysuccinimide ester of acrylic acid and the resultant monomerized reactant copolymerized with N-isopropylacrylamide.

107. The method of claim 103 wherein said first reactant is conjugated to the N-hydroxysuccinimide ester of vinyl benzoate and the resultant monomerized reactant copolymerized with N-isopropylacrylamide.

108. A method for determining the presence and/or concentration of an analyte in a biological fluid sample, comprising:
 conjugating a first reactant which is capable of specifically binding with said analyte to a temperature-sensitive polymer to form a polymer/reactant conjugate;
 conjugating a second reactant which is capable of specifically binding with said analyte to a reporter to form a reporter/reactant conjugate;
 admixing in solution said polymer/reactant and said biological fluid sample suspected of containing said analyte at a temperature other than that at which said polymer will precipitate such that specific binding occurs between said first reactant and said analyte, thereby forming a binary complex;
 adjusting the salt concentration of the admixed polymer/reactant and analyte containing sample solution to a concentration sufficient to alter the critical solution temperature of the polymer, such that said complex precipitates from the solution;
 separating said precipitated binary complex from the solution;
 resolubilizing the precipitated binary complex;
 admixing in solution said binary complex and said reporter/reactant conjugate at a temperature other than that at which said polymer will precipitate, such that specific binding occurs between said second reactant and said analyte, thereby forming a ternary complex;
 adjusting the salt concentration of the ternary complex containing solution to a concentration sufficient to alter the critical solution temperature of the polymer, such that said ternary complex precipitates from the solution; and
 measuring the amount of reporter activity in the precipitated ternary complex or in the solution and therefrom determining the presence and/or concentration of said analyte.

109. A method for determining the presence and/or concentration of an analyte in a biological fluid sample, comprising:
 conjugating a first reactant which is capable of specifically binding with said analyte to a temperature-sensitive polymer characterized by a critical solution temperature to form a polymer/reactant conjugate;
 conjugating a second reactant which is capable of specifically binding with said analyte to a reporter to form a reporter/reactant conjugate;
 admixing in solution said polymer/reactant and said biological fluid sample suspected of containing said analyte at a temperature other than that at which said polymer will precipitate such that specific binding occurs between said first reactant and said analyte, thereby forming a binary complex;
 incubating the admixed polymer/reactant and analyte containing sample solution at a temperature sufficient to cause said complex to precipitate from the solution;
 separating said precipitated binary complex from the solution;
 resolubilizing the precipitated binary complex;
 admixing in solution said binary complex and said reporter/reactant conjugate at a temperature other than that at which said polymer will precipitate, such that specific binding occurs between said second reactant and said analyte, thereby forming a ternary complex;
 incubating the ternary complex containing solution at a temperature sufficient to cause said ternary complex to precipitate from the solution; and
 measuring the amount of reporter activity in the precipitated ternary complex or in the solution and therefrom determining the presence and/or concentration of said analyte.

* * * * *